United States Patent [19]

Okamoto et al.

[11] Patent Number: 5,496,937

[45] Date of Patent: Mar. 5, 1996

[54] POLYSACCHARIDE SUBSTANCES, PROCESS FOR PRODUCING THEM AND USE OF THEM

[75] Inventors: Yoshio Okamoto, Nagoya; Naoki Enomoto, Aichi; Sachiko Furukawa, Chiryu; Yasushi Ogasawara, Hekinan; Hirofumi Akano, Handa; Yoshiya Kawamura, Khonan, all of Japan

[73] Assignee: Nakano Vinegar Co., Ltd., Handa, Japan

[21] Appl. No.: 239,760

[22] Filed: May 9, 1994

[30] Foreign Application Priority Data

May 14, 1993 [JP] Japan ..................... 5-135170

[51] Int. Cl.⁶ .............. B01D 15/08; C08B 33/02; G01N 30/48
[52] U.S. Cl. .............. 536/124; 210/198.2; 210/635; 210/636; 502/401; 502/402; 536/1.11; 536/4.1; 536/18.7; 536/22.1; 536/115
[58] Field of Search ................. 536/1.11, 4.1, 536/18.7, 22.1, 115, 124; 210/198.2, 635, 636; 502/401, 402

[56] References Cited

U.S. PATENT DOCUMENTS

| | | | |
|---|---|---|---|
| 5,051,500 | 9/1991 | Elmore | 536/124 |
| 5,071,978 | 12/1991 | Sau | 536/124 |
| 5,104,547 | 4/1992 | Cabrera et al. | 210/656 |
| 5,137,627 | 8/1992 | Feibush | 210/198.2 |
| 5,371,208 | 12/1994 | Kozulic | 536/1.11 |

FOREIGN PATENT DOCUMENTS

| | | |
|---|---|---|
| 0386926 | 9/1990 | European Pat. Off. . |
| 0445604 | 9/1991 | European Pat. Off. . |

OTHER PUBLICATIONS

Abstract, Derwent Publications Ltd., London, GB; AN 009299 of JP-A-62 270 602 (Daicel Chem. Ind. KK.), Nov. 1987.
Abstract, Derwent Publications Ltd., London, GB; AN 116634 of JP-A-63 063 696 (Agency of Ind. Sci. Echn.), Mar. 1988.
Abstract, Derwent Publications Ltd., London, GB; AN 01650 of JP-A-62 277 149 (Daicel Chem. Ind. KK.) Dec. 1987.
Patent Abstracts of Japan, vol. 12 No. 165 (C-496), May 1988 of JP-A-62 277 149.
Elisabeth Kallin et al, "New Derivatization and Separation Procedures for Reducing Oligosaccharides", Glycoconjugate J. 1986 3, pp. 311–319.
Kazukiyo Kobayashi et al, "Synthesis and Functions of Polystyrene Derivatives Having Pendant Oligosaccharides", Polymer Journal, vol. 17, No. 4, pp. 567–575 (1985).
Shinichi Kitamura et al, Starch Chemistry, vol. 36, No. 4, pp. 257–264 (1989).
Yoshio Okamoto et al, "Useful Chiral Stationary Phases for HPLC", Chemistry Letters, pp. 1857–1860 (1987).

*Primary Examiner*—Ronald W. Griffin
*Attorney, Agent, or Firm*—Frishauf, Holtz, Goodman, Langer & Chick

[57] ABSTRACT

A polysaccharide substance having the following formula is provided:

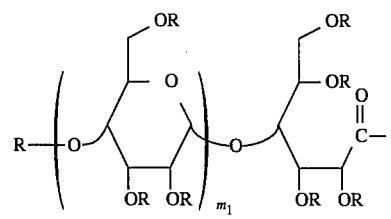

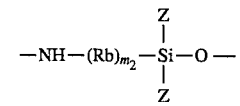

inner and outer surface of a porous carrier

Also provided is a method of producing the polysaccharide substance in which an oligosaccharide having a degree of polymerization from 3 to 10 is chemically bonded to a silane agent at the reducing terminal of the resultant oligosaccharide, the oligosaccharide compound is then polymerized to an average degree of polymerization from 11 to 500 in the presence of an enzyme. Another method for producing the polysaccharide substance is provided in which an aldehyde group at the reducing terminal of an oligosaccharide having a degree of polymerization from 3 to 10 is oxidized with an oxidizing agent, and the saccharide chain of the oxidized product is polymerized to a degree of polymerization from 11 to 500 in the presence of an enzyme, followed by the addition of an acid. The polysaccharide substance has excellent solvent resistance and is useful as a separating agent for chromatography, especially for the separation of chiral compounds.

22 Claims, 4 Drawing Sheets

POLYSACCHARIDE SUBSTANCES, PROCESS FOR PRODUCING THEM AND USE OF THEM

FIELD OF THE INVENTION

The present invention relates to novel substances, methods of producing them and use of them. More particularly, it relates to novel substances in which a polysaccharide is chemically bonded to silica gel at its reducing terminal alone and in which part or all of the hydroxyl groups in the polysaccharide moiety are substituted with a particular substituent, as well as to methods of producing them and to a separating agent for use in chromatography containing the same.

BACKGROUND OF THE INVENTION

It has hitherto been known that a substance consisting of silica gel physically carrying a polysaccharide, such as cellulose, amylose or a derivative thereof, is useful as a separating agent for use in chromatography, in particular, as a separating agent for optical resolution.

However, due to its poor solvent resistance, the substance suffers from the drawback that a usable eluent is limited at the time when it is to be used in liquid chromatography, or the like. In addition, it is not possible to fully utilize the usefulness of the polysaccharide. There is also a limitation in solvents usable for the washing of contaminated columns, which can be a cause for the deterioration of columns.

In order to solve such problems, it has been proposed to use a compound in which a polysaccharide is chemically bonded to silica gel. However, in this case, it is not possible to select the site at which the chemical bonding to silica gel takes place. This exerts influences on the higher structure of the polysaccharide per se and the usefulness of the polysaccharide is diminished. In addition, there occurs still another problem that the silica gel compound thus obtained shows a big difference in quality since the bonding does not take place at a specific site.

The present inventors have carried out investigations on the use of a separating agent of the structure wherein silica gel is used as a porous carrier and polysaccharides are chemically bonded to the inner and outer surfaces of the pores of the silica gel at the reducing terminals of the polysaccharides. The present inventors have lactonized the reducing terminals of oligosaccharides and performed a reaction of the lactonized product with, for example, 3-aminopropyltriethoxysilane, to obtain a product containing a saccharide chain chemically bonded via an amide bond to a silane agent, as shown by the following Formula A:

Formula A [Formula No. 4]

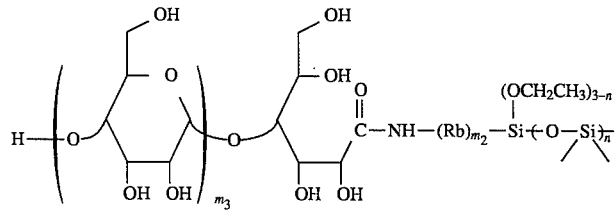

(wherein Rb represents a substituted or unsubstituted methylene group, a substituted or unsubstituted phenylene group or a group containing covalently bonded hetero atom(s); $m_2$ represents an integer of from 1 to 20; $m_3$ represents an integer of from 2 to 9; and n represents an integer of from 0 to 3, preferably 0). Part of the silane agents may be in a polymerized state.

The present inventors have also developed a method of polymerizing saccharide chains and succeeded, by using the method, in polymerizing the saccharide moieties of the compound represented by Formula A to an arbitrary polymerization degree by an enzymatic reaction using the compound as a primer. Further, the inventors have succeeded in obtaining compounds represented by Formula B set forth below, by allowing a polysaccharide derivative of a silane agent obtained by an enzymatic synthesis to bind to silica gel at the silane moiety.

Formula B [Formula No. 5]

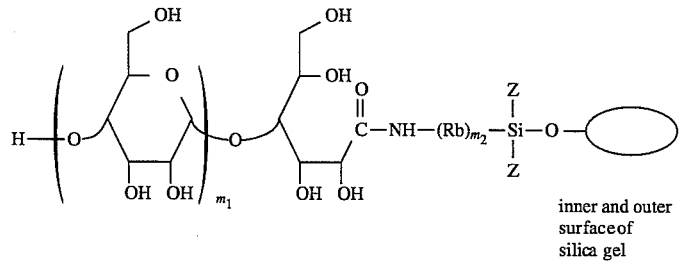

inner and outer surface of silica gel (wherein Z represents a member selected from the group consisting of the surface of a porous carrier, a halogen atom, an alkyl group, an alkoxy group, a phenyl group, a silane agent and a saccharide-bonded silane agent; $m_1$ represents the number of monosaccharide units, which may be in the range of from 10 to 500 on average; and Rb and m2 have the same meanings as defined above).

The compounds represented by Formula (1) according to the invention have been obtained by substituting part or whole of the hydroxy groups in the saccharide moiety of the compound represented by Formula B with, for example, an isocyanate derivative, or the like.

Formula (1) [Formula No. 6]

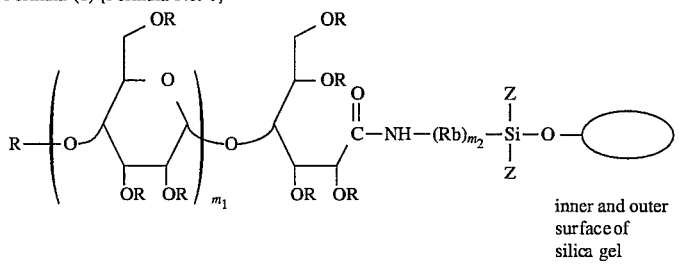

inner and outer surface of silica gel

Alternatively, the compounds represented by the above Formula B have been obtained in the following manner: The reducing terminal of an oligosaccharide is oxidized to a glucanate, and its saccharide moiety is polymerized to an arbitrary degree of polymerization with the action of an enzyme, using the glucanate as a primer. An acid is added to the resulting reaction mixture to effect lactonization. The lactonized polysaccharide is then allowed to bond via amide bond to a surface-treated silica gel having amino groups on its surface.

The compounds represented by the above Formula (1) have also been obtained by substituting part or whole of the hydroxyl groups in the saccharide moiety of the compounds of Formula B obtained as above with, for example, an isocyanate derivative, or the like.

In the thus synthesized compounds of Formula (1), saccharides are chemically bonded via a silane agent to the inner and outer surface of the pores of a porous carrier, such as silica gel, only at the 1positioned carbon in the reducing terminal of the saccharide moiety. It has been found that the novel compounds are capable of solving the above-mentioned problems, and the present invention has been completed on the basis of the finding.

SUMMARY OF THE INVENTION

Accordingly, there is provided in accordance with the present invention a novel substance having a main structure of the following Formula (1) in which a polysaccharide or a derivative thereof is chemically bonded to the inner and outer surfaces of a porous carrier at the reducing terminal of said polysaccharide or derivative thereof.

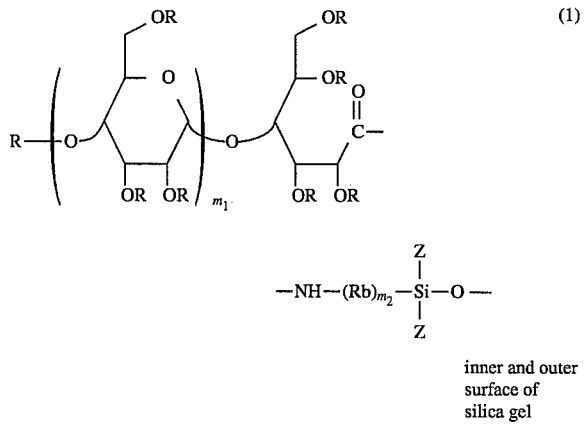

inner and outer surface of silica gel

[wherein R represents Ra, —CO—Ra or —CO—NH—Ra (in which Ra represents a hydrogen atom or a substituent selected from the group consisting of a substituted or unsubstituted alkyl group, a substituted or unsubstituted phenyl group and a substituted or unsubstituted heterocyclic residue); on the point of improving separation ability remarkably, substitution rate of R is preferably 30 to 100%. Rb represents a substituted or unsubstituted methylene group, a substituted or unsubstituted phenylene group or a group containing covalently bonded hetero atom(s); Z represents a member selected from the group consisting of the surface of a porous carrier, a halogen atom, an alkyl group, an alkoxy group, a phenyl group, a silane agent and a saccharide-bonded silane agent; $m_1$ represents the number of monosaccharide units, which may be in the range of from 10 to 500 on average; and m2 represents an integer of from 1 to 20].

Also provided are a method of producing the novel substance of the above Formula (1) in which an oligosaccharide having a degree of polymerization from 3 to 10 is chemically bonded to a silane agent at the reducing terminal of the oligosaccharide, the oligosaccharide derivative obtained is extended to an average degree of polymerization from about 11 to about 500 by the action of an enzyme, and then the resulting polysaccharide is chemically bonded to a porous carrier at the silane moiety present at the terminal of the polysaccharide; a method of producing the novel substance of the above Formula (1) in which the aldehyde group present at the reducing terminal of an oligosaccharide having a degree of polymerization from 3 to 10 is oxidized with an oxidizing agent, and the saccharide chain of the oxidized product is polymerized to a degree of polymerization about 11 to about 500 by the action of an enzyme, followed by the addition of an acid; and a separating agent for chromatography comprising the novel substance represented by Formula (1).

DETAILED DESCRIPTION OF THE INVENTION

Figure 1:
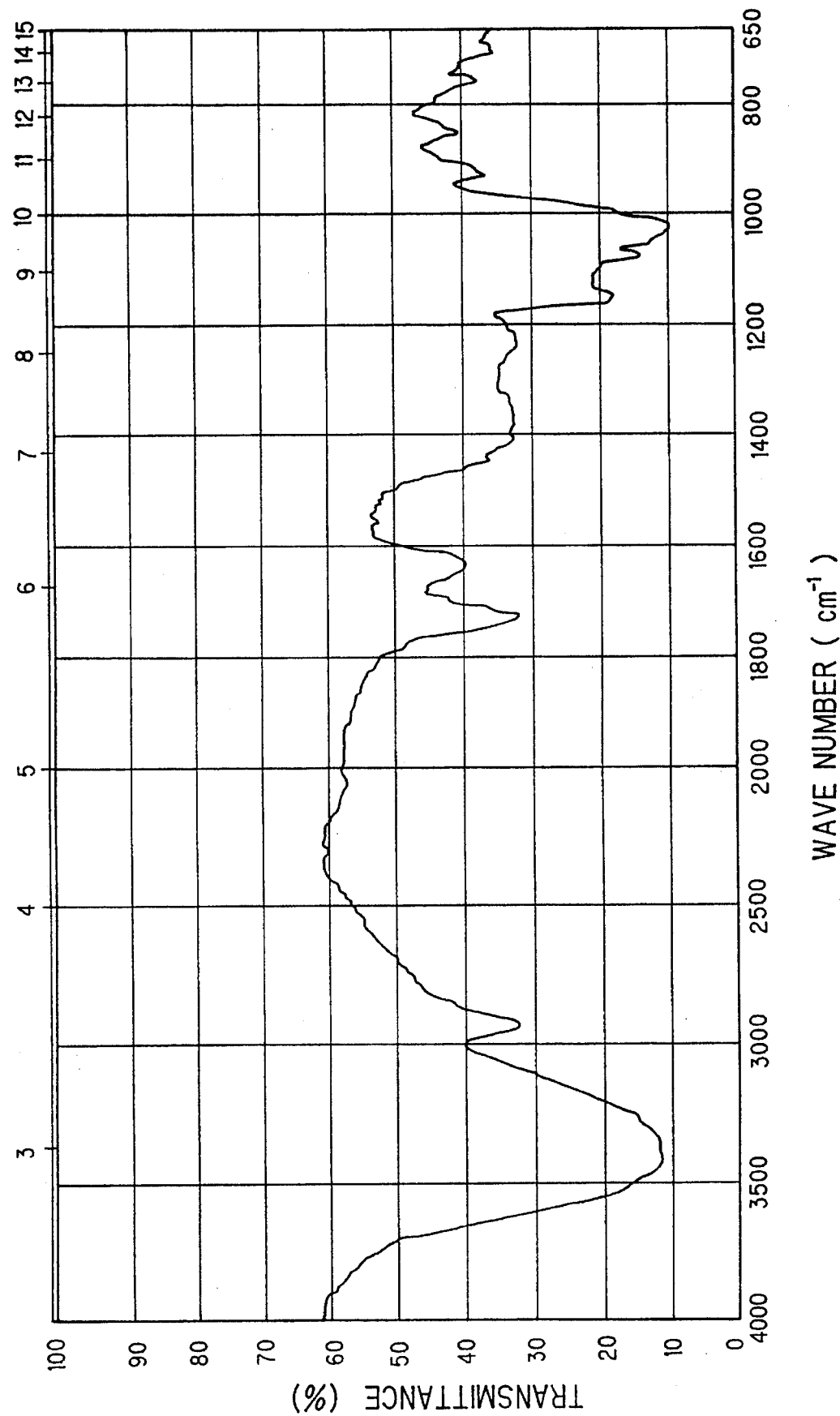
FIG. 1 is an IR spectrum of {o-α-D-glucopyranosil-(1→4)}$_4$-D-gluconolacton (which may hereinafter be referred to as lactone) obtained in Production Example 1.

Any oligosaccharide can be used in the present invention, including synthetic oligosaccharides, naturally-occurring oligosaccharides and derivatives thereof, provided that a polysaccharide can be synthesized by using the oligosaccharide as a substrate in an enzymatic synthesis. Specific examples of usable oligosaccharides include α-1,4-glucan oligomers (maltooligosaccharides), β-1,4-glucan oligomers (cellooligosaccharides), α-1,6-glucan oligosaccharides (isomaltooligosac charides), β-1,6-glucan oligomers (gentiooligosaccharides), α-1,3-glucan oligomers (nigerooligosaccharides), β-1,3-glucan oligomers (laminalioligosaccharides), α-1,2-glucan oligomers, β-1,2-glucan oligomers (sophorooligosaccharides), β-1,4-chitooligosaccharides, β-1, 4-N-acetylchitooligosaccharides, β-1,4-galactans (lactooligosaccharide s), α-1,6-galactans (melioligosaccharides), β-2,1-fructans (inulooligosaccharides), β-2,6-fructans, β-1,4-xylans, β-1,3-xylans, β-1,4-mannans, α-1,6-mannans, and the like.

These oligosaccharides have a number average degree of polymerization 3 or more, and there is no particular upper limit on the degree of polymerization. However, a degree of polymerization of 3 to 10 can be preferred with regard to reactivity upon lactonization or reductive amination, and to easiness of handling.

Examples of enzymes usable in the invention include hydrolases, saccharide transferases, polymerases, and the like. Any enzyme capable of synthesizing a polysaccharide from an oligosaccharide can be used, and microorganisms containing such an enzyme can also be used. Specific examples include phosphorylase, dextransucrase, levansucrase, pullulanase, and microorganisms capable of producing these enzymes.

The polysaccharides have a mean degree of polymerization 11 or more. Although there is no particular upper limit, a mean degree of polymerization 500 or less is usually preferred.

In the present invention is used a porous carrier, such as porous inorganic carriers and porous organic carriers.

Specific examples of usable porous carriers include porous inorganic carriers, such as silica gel, diatomaceous earth, porous glass, hydroxyapatite, alumina, titanium oxide, magnesia, etc.; and porous organic carriers, such as polyacrylamides, polyacrylates, etc. Of these carriers, silica gel is particularly preferred. Silica gel may have a particle size of from 1 to 1,000 μm, preferably from 2 to 100 μm, and a mean pore size from 10Å to 100 μm, preferably from 2 nm to 500 nm.

When a porous membrane is used as the porous carrier, it is possible to obtain a novel separating membrane.

As the silane agent is used an amino group-containing compound. In cases where the reducing terminals are lactonated or are reduced in the presence of a reducing agent to effect amination, a primary amine-containing silane agent can be preferred. Any commercially available silane coupling reagents and synthetic silane agents modified to have amine(s) can be used as the silane agent.

It is also possible to employ a spacer capable of bonding a silane agent and a polysaccharide, such as a compound having two or more functional groups of either the same or different kinds, one functional group of said compound being capable of forming a chemical bond with the reducing terminal of a saccharide and the other (or another) functional group of said compound being capable of forming a chemical bond with a silane agent. Examples of such functional groups include vinyl, amino, hydroxyl, carboxyl, aldehyde, isocyanate, isothiocyanate, thiol, silanol, epoxy, ether, ester and amide groups, as well as halogen atoms. Any silane agents capable of bonding to these functional groups can be used. Typical examples of silane agents are set forth below. In the above Formula (1), Rb represents a substituted or unsubstituted methylene group, a substituted or unsubstituted phenylene group or a group containing covalently bonded hereto atom(s). Typically, Rb corresponds to part of side chains of silane agents, such as those set forth below, or to part of a moiety formed by chemical bonding between a spacer and a silane agent.

[Formula 10]

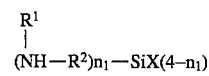

[Formula 11]

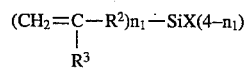

[Formula 12]

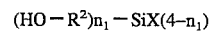

[Formula 13]

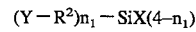

[Formula 14]

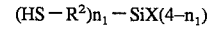

[Formula 15]

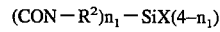

[Formula 16]

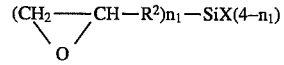

[Formula 17]

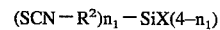

In the above formulae, $n_1$ represents an integer of from 1 to 3; $R^1$ represents a hydrogen atom, an alkyl chain having from 1 to about 20 carbon atoms or a derivative thereof; $R^2$ represents an alkyl chain having from 1 to about 20 carbon atoms or a derivative thereof; X represents a substituted or unsubstituted alkoxy group having from 1 to 10 carbon atoms, a halogen atom (preferably chlorine atom), a hydroxyl group or a substituted or unsubstituted phenoxy group, at least one X being a substituted or unsubstituted alkoxy group, a halogen atom, a hydroxyl group and a substituted or unsubstituted phenoxy group; and Y represents a halogen atom.

The substituent R introduced into part or all of the hydroxyl groups in the polysaccharide moiety of the compounds represented by the above Formula (1) is to modify the hydroxyl groups. Two or more substituents of different kinds may be introduced into the hydroxyl groups of one polysaccharide moiety. Ra of the substituent R is selected from substituted or unsubstituted alkyl groups, substituted or unsubstituted phenyl groups and substituted or unsubstituted heterocyclic residues. Specific examples of substituents Ra include methyl, ethyl, propyl, t-butyl, phenyl, methylphenyl, dimethylphenyl, ethylphenyl, diethylphenyl, trimethylsilylphenyl, alkoxyphenyl, dialkoxyphenyl, halogenated phenyl, dihalogenated phenyl, phenylazophenyl, naphthyl, anthryl, pyridyl and furyl groups.

Methods of producing compounds in which a silane agent is chemically bonded to an oligosaccharide (hereinafter referred to as Compound A or A') will be explained hereinbelow, taking maltopentose as an example of oligosaccharide.

A KOH-methanol solution is added to an iodine-methanol solution of maltopentose to obtain potassium {0-α-D-glucopyranosyl-$(1\rightarrow 4)\}_4$-D-glucanate. The potassium ion of the glucanate is exchanged with a hydrogen ion by a known method using an ion exchange resin (H-type) to obtain {0-α-D-glucopyranosyl-$(1\rightarrow 4)\}_4$-D-glucono-1,5-lactone. The lactone is then reacted, for example, with 3-aminopropyltriethoxysilane in ethylene glycol to obtain a desired compound (Compound A). This reaction is based on the process described in Polymer Journal, Vol. 17, No. 4, p. 567–575 (1985). It is necessary to use anhydrous ethylene glycol and to perform the reaction in a nitrogen stream, so that the reaction could proceed under a moisture free condition.

Alternatively, the reducing terminal of the oligosaccharide is reacted with a primary amine, for example, 3-aminopropyltriethoxysilane, to form a Schiff's base. It is then reduced to a secondary amine in the presence of a reducing agent, to obtain a desired compound (Compound A') [See Elizabeth Kallin, Glycoconjugate J. (1986), 3, 311–319].

Methods of producing compounds of Formula Bs of the present invention will be explained hereinbelow.

according to a known silane-treating method, to obtain Compound Bs.

(2) Alternatively, Compound A is chemically bonded to silica gel by a known silane-treating method. The resulting compound is then reacted, for example, with 4-methylphenyl isocyanate in a mixture of dimethylacetamide and pyridine to effect substitution of all or part of the hydroxy groups of the oligosaccharide.

In the present invention, any of the above methods (1) and (2) can be employed. In the case where the amount of compounds bonded to silica gel is to be increased, method (2) can be preferred. The amount of compound A or A' bonded to silica gel is preferably from 5 to 50% by weight, based on the weight of silica gel. However, the amount is not necessarily limited to the above range.

The thus obtained Compound Bs can be subjected to an end capping treatment according to a known method, so as to remove the influence of remaining silanol groups.

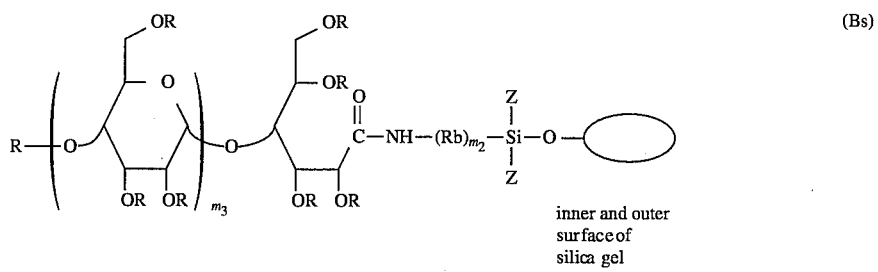

(Bs)

inner and outer surface of silica gel (wherein Z represents a member selected from the group consisting of the surface of a porous carrier, a halogen atom, an alkyl group, an alkoxy group, a phenyl group, a silane agent and a saccharide-bonded silane agent; ms represents the number of monosaccharide units, which may be in the range from 2 to 9 on average; and Rb and $m_2$ have the same meanings as defined above).

(1) Compound A obtained as above is reacted, for example, with 4-methylphenyl isocyanate in a mixture of dimethylacetamide and pyridine to substitute all or part of the hydroxyl groups of the oligosaccharide. This reaction can be carried out according to a known method. The resulting compound is then chemically bonded to silica gel The introduction of the above substituents into the hydroxyl groups in the saccharide moieties of compounds represented by Formula Bs can be effected by any known method.

Methods of producing the novel compounds of Formula (1) of the present invention will be illustrated hereinbelow.

Process 1

Reaction (1):

A method of synthesizing compounds represented by Formula A and Formula A' set forth below will be illustrated.

Formula 18

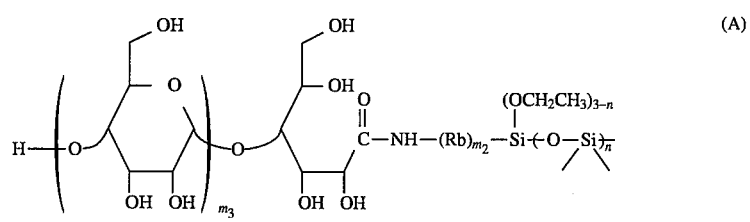

[Formula 19]

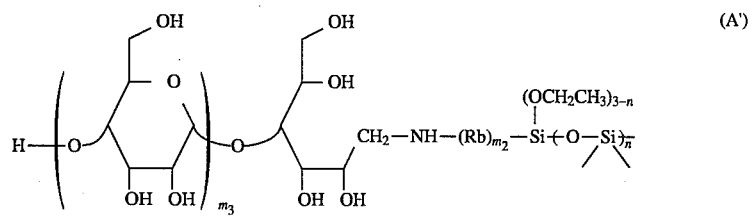

(wherein Rb, $m_2$, $m_3$ and n have the same meanings as defined above).

Compounds represented by the above Formula A can be synthesized by lactonizing an oligosaccharide and then forming an amide bond with a silane agent, for example, by referring to the description of Japanese Patent Application No. H4-311,042 (311,042/1992). In this case, the reaction is preferably carried out under a moisture free condition since polymerization between silane agents takes place if water is present in the reaction mixture. Chemical bonding between oligosaccharides and silane agents can also be formed by allowing an oligosaccharide to chemically bond to an amino group-containing silane agent in the presence of a reducing agent, without lactonizing the reducing terminal of the oligosaccharide production of compounds represented by Formula A'. In the formula, n represents an integer of 0 to 3, preferably 0 (part of the silane agents may be polymerized up to a number of n), and $m_3$ represents an integer of 2 to 9 [see Elizabeth Kallin et al., Glycoconjugate J., 3, 311–319 (1986)]. Examples of reducing agents usable in the above production include borane compounds, such as $NaBH_4$, $NaBH_3CN$, borane-pyridine complex, borane-dimethylamine complex, borane trimethylamine, and the like. It is also possible to be chemically bonded to a silane agent via a spacer at the reducing terminal of the saccharide. That is to say, the reducing terminal of a saccharide can be subjected to amide bonding or reductive amination with one functional group (for example, an amino group) contained in the spacer, and then the spacer can be chemically bonded with a silane agent.

The enzymatic synthesis can be conducted at a temperature of from room temperature to 55° C., preferably 35° to 45° C. in sterilized water or in malate buffer, etc. by using a compound represented by Formula A or A', phosphorylase (enzyme) and potassium salt of glucose-1-phosphate (substrate) at a pH of 5 to 8, preferably 6 to 7. The pH is adjusted with hydrochloric acid, potassium hydroxide, or the like. It can be preferred, for the prevention of polysaccharide degradation, to add 10 to 30% (W/W) of dimethylsulfoxide (DMSO) in cases where a compound having a mean degree of polymerization 30 or more is to be synthesized. The mean degree of polymerization ($m_1$) can be determined by measuring phosphoric acid liberated from glucose-1-phosphate, or an approximate value can be obtained from a standard curve of the GPC, using a commercially available amylose (produced and marketed by Nakano Vineget Co., Ltd.). The reaction is stopped by deactivating the enzyme at an arbitrary degree of polymerization ($m_1$). The polysaccharide derivatives are precipitated in ethanol, washed with ether, hexane, etc. and dried under reduced pressure, to obtain compounds represented by the following Formula C or C':

[Compound 20]

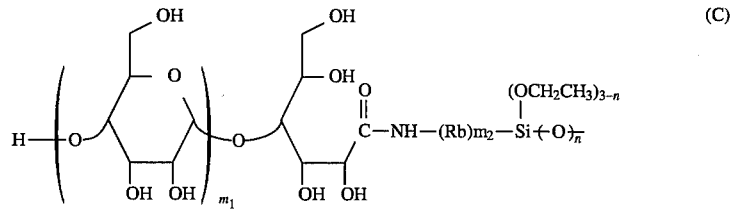

(wherein Rb and $m_1$ have the same meanings as above; and n is an integer of from 0 to 3, preferably 3. Part of the ethoxy groups may be eliminated during the enzymatic synthesis).

[Compound 21]

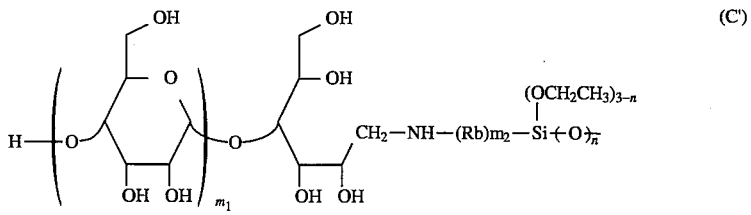

(wherein Rb, $m_1$ and n have the same meanings as above).

Reaction (3):

The bonding between a compound of Formula C or C' obtained in Reaction (2) and silica gel will be illustrated.

A compound represented by Formula C or C' is dissolved into anhydrous DMSO, anhydrous LiCl-DMA solution, or the like. Pyridine as a catalyst is added thereto, and the compound is bonded to silica gel at the silane moiety of the compound by a conventional silane-treating method, to obtain a compound represented by the following Formula B or B':

Reaction (2):

A method of enzymatically synthesizing the saccharide moiety of compounds of Formula A or A' obtained in (1) will then be illustrated.

In cases where the saccharide chain of the compounds of Formula A or A' prepared by using maltooligosaccharides having 4 or more saccharide units is enzymatically synthesized, phosphorylase can be used as an enzyme. For example, phosphorylase derived from potato can be used [see Starch Chemistry, Vol. 36, No. 4, p. 257–264 (1989)].

[Compound 22]

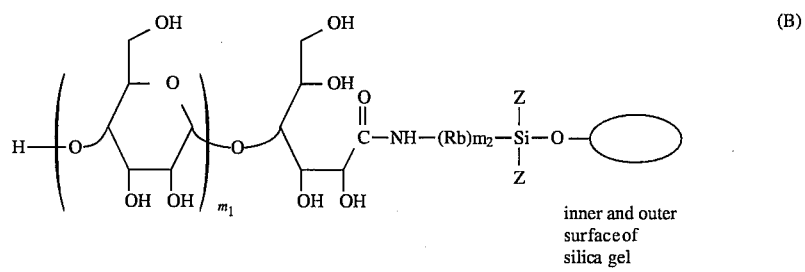

(B)

inner and outer surface of silica gel

[Compound 23]

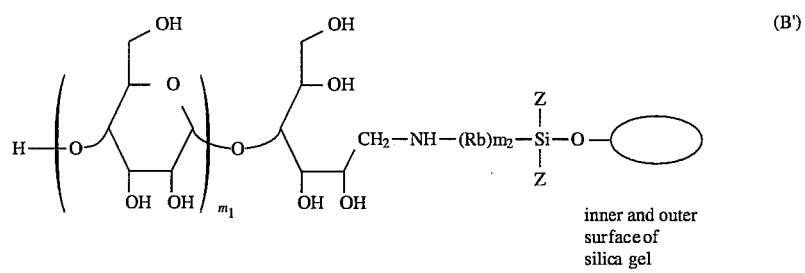

(B')

inner and outer surface of silica gel (wherein Rb, Z, $m_1$ and $m_2$ have the same meanings as defined above).

Process 2

Reaction (1):

Production of a polysaccharide derivative having a lactonized reducing terminal (which may hereinafter be referred to as lactonized polysaccharide) will be illustrated.

The oligosaccharide chain of a glucanate salt obtained by oxidizing the reducing terminal of an oligosaccharide [Japanese Patent Application No. H4-311,042 (311,042/1992)] is polymerized by enzymatic synthesis, and the reducing terminal is then lactonized. For example, when a maltooligosaccharide is used as an oligosaccharide, the enzymatic synthesis is carried out at a temperature of from room temperature to 55° C., preferably 35° to 45° C. in sterilized water or in malate buffer, etc., using a glucanate solution obtained by the oxidation of the reducing terminal as a primer, phosphorylase as an enzyme, and potassium salt of glucose-1-phosphate as a substrate. At a pH of 5 to 8, preferably 6 to 7. The pH is adjusted with hydrochloric acid, potassium hydroxide, or the like. It can be preferred, for the prevention of polysaccharide degradation, to add 10 to 30% (W/W) of dimethylsulfoxide (DMSO) when a compound having a mean degree of polymerization 30 or more is to be synthesized. The mean degree of polymerization ($m_1$) can be determined by measuring phosphoric acid liberated from glucose-1-phosphate, or an approximate value can be obtained from a standard curve of the GPC, using commercially available amylose (produced and marketed by Nakano Vineget Co., Ltd.). The reaction is stopped by inactivating the enzyme at an arbitrary degree of polymerization ($m_1$). Thereafter, the terminal of the resulting polysaccharide is lactonized by reducing its pH to 0 to 4, preferably 1 to 2 with the addition of a strong acid, such as hydrochloric acid, or the like. The polysaccharide derivative is precipitated in ethanol, washed with ether, hexane, etc. and then dried under reduced pressure, to obtain amylose having a lactonized reducing terminal (which may hereinafter be referred to as lactonized amylose).

After a lactonized polysaccharide has been obtained, it can be bonded to the amino group of a spacer by forming an amide bond. It is also possible to carry out the enzymatic synthesis after the reducing terminal of an oligosaccharide has been lactonized and a spacer has been attached thereto.

Reaction (2):

Bonding between a lactonized polysaccharide and a surface-treated silica gel will be illustrated.

Any conventional method can be used for the treatment of inner and outer surfaces of the pores of silica gel with a silane agent having an amino group, such as 3-aminopropyl-triethoxysilane. The lactonized polysaccharide obtained in the above Reaction (1) is dissolved into a solvent, such as DMSO, and an amide bond is formed by allowing the lactonized polysaccharide to react with an amino group functionalized silica gel at 50° to 70° C. Then, excess lactonized polysaccharide is removed by washing with DMSO, acetone, hexane or the like, and the reaction product is dried under reduced pressure to obtain a compound represented by the above-mentioned Formula B.

In cases where a polysaccharide bonded with a spacer as mentioned in Reaction (1) is used, the surface of silica gel can be treated with (a) a silane agent capable of bonding with the spacer, or (b) a derivative of a silane agent modified to acquire the capability of bonding with the spacer.

Process 3

The hydroxyl groups in the saccharide moieties of the compounds of Formula B or B' obtained by the above-described Process 1 or 2 are reacted, for example, with 4-methylphenyl isocyanate or 3,5-dimethylphenyl isocyanate or 3,5-dichlorophenyl isocyanate or phenyl isocyanate in an anhydrous DMA/pyridine solution or anhydrous DMSO/pyridine solution, to substitute all or part of the hydroxyl groups in the saccharide moieties of the compounds. This reaction can be performed according to a known method.

There are no particular limitations on the amount of polysaccharide derivatives chemically bonded to silica gel. However, the amount of from 5 to 50% by weight is usually preferred. The thus obtainable compounds of the present invention can be subjected to an end capping treatment according to a known method, so as to remove the influence of remaining silanol groups and to improve their properties as a separating agent.

In illustrating the chemical structures of the compounds according to the present invention, part of the structures indicating the positions of hydroxyl groups in saccharide moieties or the like is partly omitted or simplified for convenience sake and to meet the universality of the compounds.

EXAMPLES

The present invention will be explained in more detail by means of examples.

Production Example 1 Synthesis of Compound $A_1$
($m_3$=4 in Compound A)

Into 30 ml of methanol was dissolved 4.0 g of iodine, and a solution prepared by dissolving 6 g of maltopentose into an appropriate quantity of distilled water was added thereto. Then, 100 ml of 4% KOH-methanol solution was dropped thereto, and the resulting mixture was stirred at 40° C. for 30 minutes. The reaction mixture was cooled on an ice bath to form precipitate, which was then collected by filtration and dissolved into 100 ml of distilled water. Subsequently, powder of activated carbon was added thereto to remove excess iodine, the resulting mixture was subjected to filtration, and the filtrate was freeze-dried.

The freeze-dried product was dissolved into 40 ml of distilled water and was treated with 80 mg-eq. of Amberlite 120-B (H-type). After being concentrated, the product was again freeze-dried to obtain 5.2 g of lactone. The product was identified by the C=O stretching vibration of lactone at 1,740 cm$^{-1}$ in its IR spectrum shown in FIG. 1 and a signal of 170.8 ppm in its $^{13}$C-NMR.

Figure 2:
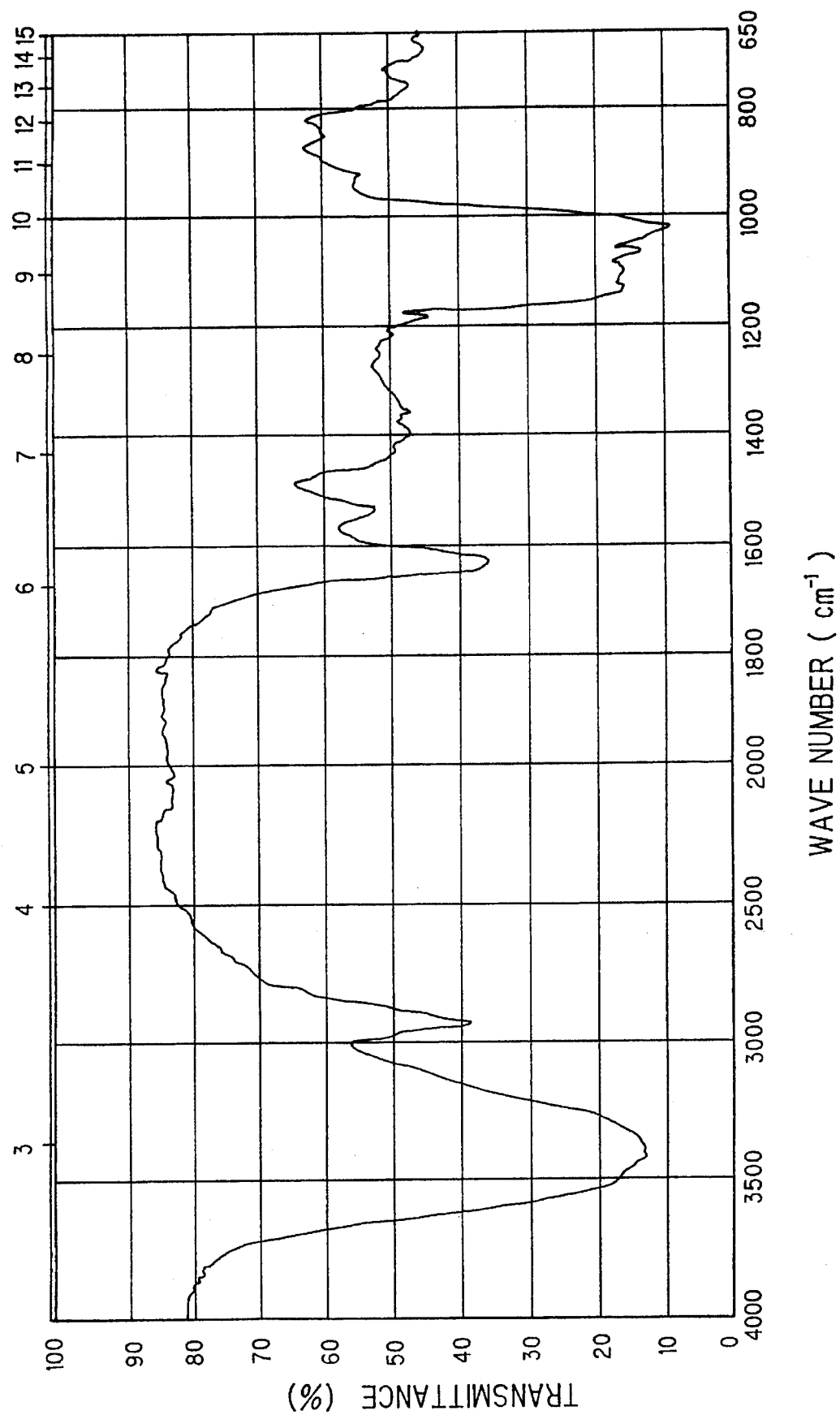
FIG. 2 is an IR spectrum of a compound represented by Formula $A_1$.

Into 7 ml of anhydrous ethylene glycol was dissolved 1 g of the thus obtained lactone. To this was added 0.55 g of 3-aminopropyltrieth oxy-silane, and reaction was allowed to proceed at 70° C. for 6 hours in a nitrogen stream. The product was precipitated in 200 ml of acetone, washed with 100 ml of acetone and dried under reduced pressure at 60° C. for 3 hours, to obtain 1.08 g of Compound $A_1$. The compound shows a peak of N—H deformation vibration of secondary acid amide at 1,540 cm$^{-1}$ and a peak of C=O stretching vibration at 1,640 cm$^{-1}$ in its IR spectrum (FIG. 2). In $^{13}$C-NMR, the compound shows a chemical shift of the carbon used for the amide bond at around 172 ppm, and a signal of the 6-position carbon shifted to lower magnetic field due to the opening of the terminal saccharide ring at around 62.7 ppm. These data show that the resultant compound has a structure shown by the above-described Compound $A_1$.

Production Example 2

Synthesis of Compound $Bs_1$ (wherein Z represents a member selected from the group consisting of the surface of a porous carrier, an alkoxy group, a silane agent and a saccharide-bonded silane agent; ms represents the number of monosaccharide units, which may be 4; and Rb represents methylene, $m_2$ represents 3 and R represents a hydrogen atom or Formula 27).

Figure 3:
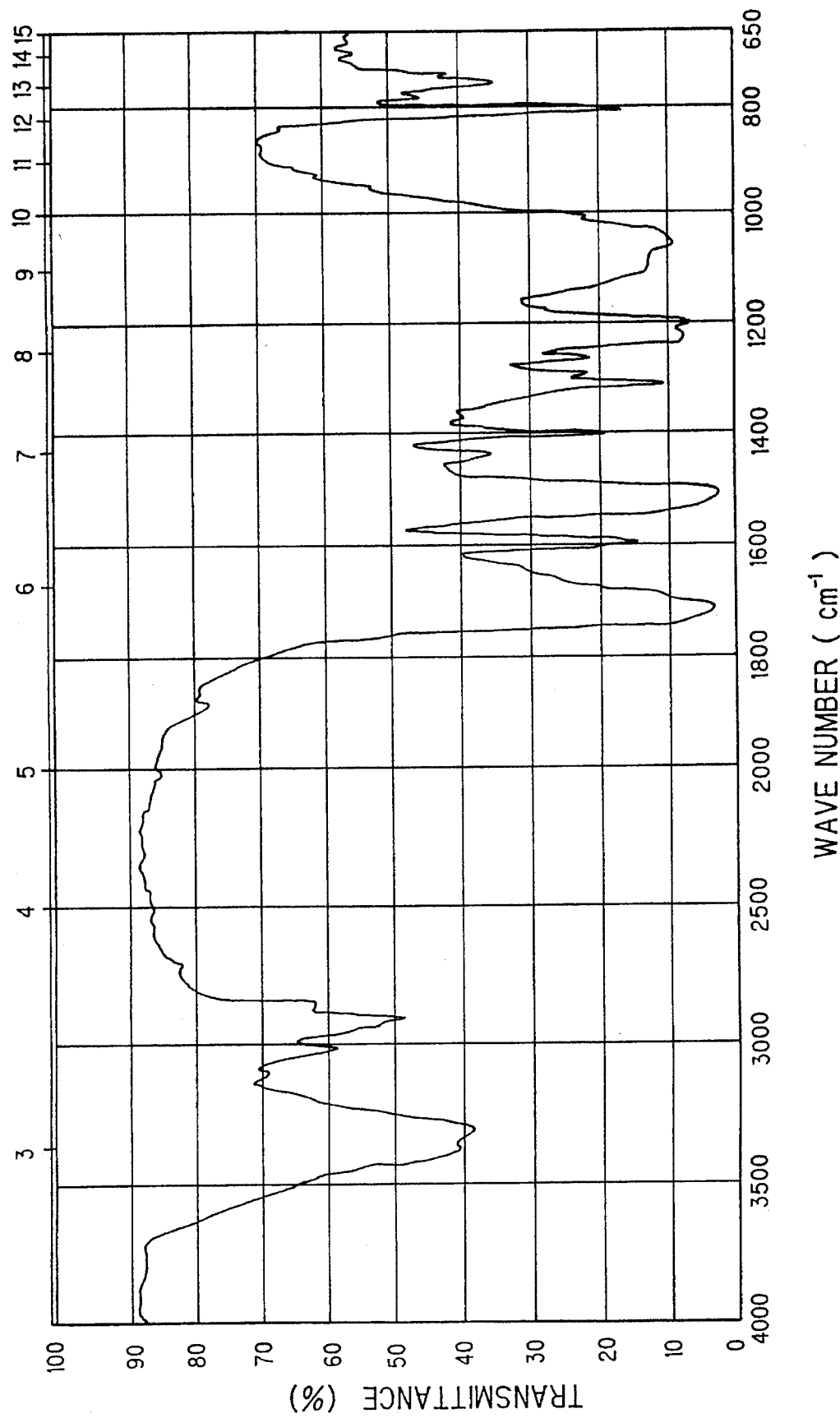
FIG. 3 is an IR spectrum of oligosaccaride tris(4-methylphenyl carbamate) derivative obtained in Production Example 2.
Figure 4:
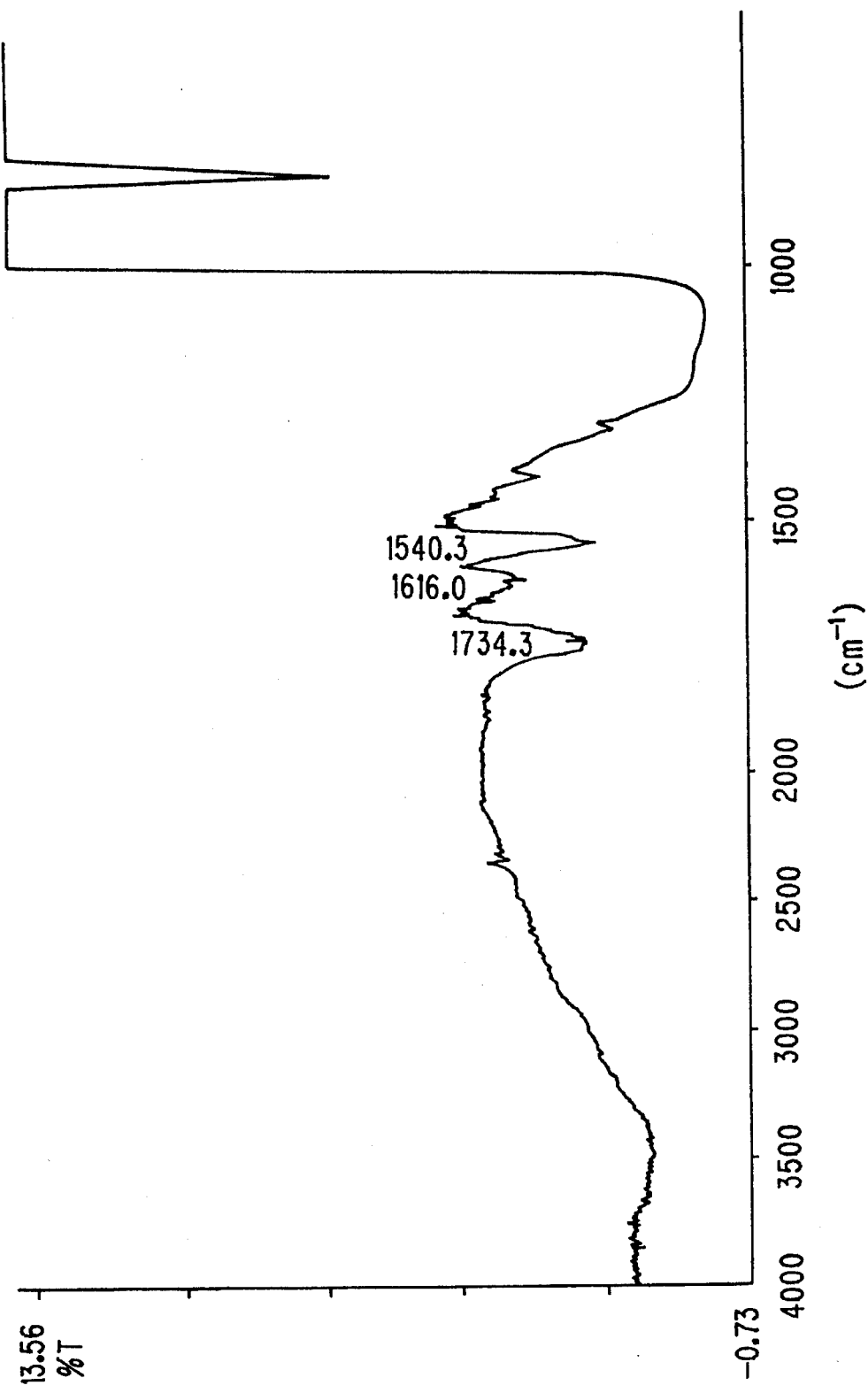
FIG. 4 is an IR spectrum of a compound represented by Formula (2).

Into a mixture of 20 ml of DMA and 5 ml of pyridine was dissolved 0.9 g of Compound $A_1$ synthesized in Production Example 1. To this was added 4 g of 4-methylphenyl isocyanate. After the resulting mixture had been stirred at 80° C. for 5 hours, the presence of excess 4-methylphenyl isocyanate in the reaction mixture was confirmed by the C=N stretching vibration at 2,270 cm$^{-1}$ in its IR spectrum. Part of the reaction mixture was taken out as a sample and was added to aqueous methanol solution to form precipitate, which was then washed and dried. The IR spectrum of the precipitate showed an absorption of C:O of the secondary carbamic acid ester at 1,710 cm$^{-1}$ (FIG. 3).

Meanwhile, the rest of the above reaction mixture was added to 3 g of previously activated silica gel (produced by YMC Co.; mean pore diameter, 120Å; mean particle size, 5 μm), and reaction was allowed to proceed at 90° C. for 12 hours. The resultant silane-treated silica gel contained in the reaction mixture was washed with tetrahydrofuran, methanol, acetone and hexane to remove the excess carbamate derivative of Compound A, not bonded to the silica gel, and then dried in vacuum at 60° C. for 2 hours. The thus obtained compound was subjected to spectrometry and elementary analysis. Results of the elementary analysis are shown in Table 1.

TABLE 1

| Separating Agent | Elementary Analysis | | |
|---|---|---|---|
| | C (%) | H (%) | N (%) |
| $Bs_1$ | 3.28 | 1.03 | 0.26 |
| $Bs_2$ | 13.99 | 2.52 | 1.16 |
| $Bs_3$ | 26.14 | 2.71 | 2.93 |

The IR spectrum showed a peak of stretching vibration of carbonyl group at 1,710 cm$^{-1}$, which proves the existence of polysaccharide derivatives on silica surface. Thus the compound $Bs_1$ was obtained. In order to improve the properties of the thus obtained Compound $Bs_1$ as a separating agent for chromatography, the compound was subjected to a conventional end capping treatment with trimethylchlorosilane.

The resulting product was collected by filtration with a G4 glass filter and was washed with tetrahydrofuran, methanol, acetone and hexane, and then dried in vacuum at 60° C. for 2 hours, to obtain a product to be used as a separating agent for chromatography.

($Bs_1$)

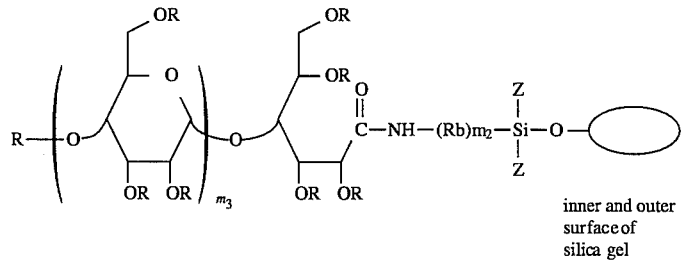

inner and outer surface of silica gel

Production Example 3 Synthesis of Compound $A_1$
($m_3$=4 in Compound A)

Into 30 ml of methanol was dissolved 4.0 g of iodine. To this was added a solution prepared by dissolving 6 g of maltopentose into an appropriate quantity of distilled water. Then, 100 ml of 4% KOH-methanol solution was dropped thereto, and the resulting mixture was stirred at 40° C. for 30 minutes. The reaction mixture was cooled on an ice bath to form precipitate, which was then collected by filtration and dissolved into 100 ml of distilled water. Subsequently, powder of activated carbon was added thereto to remove excess iodine, the resulting mixture was subjected to filtration, and the filtrate was freeze-dried.

The freeze-dried product was dissolved into 40 ml of distilled water and treated with 80 mg-eq. of Amberlite 120-B (H-type). After being concentrated, the product was freeze-dried to obtain 5.2 g of lactone. The product was identified by its IR spectrum which showed a peak of C=O stretching vibration of lactone at 1,740 cm$^{-1}$ as in FIG. 1, as well as by its $^{13}$C-NMR spectrum which showed a signal at 170.8 ppm.

Into 4.4 ml of anhydrous DMSO (dimethylsulfoxide) was dissolved 0.7 g of the thus obtained lactone. To this was added 0.25 g of 3-aminopropyltriethoxysilane, and reaction was allowed to proceed at 70° C. for 6 hours in a nitrogen stream. Part of the product (about 0.6 ml) was taken out and used as a sample for IR and NMR analyses.

In its IR spectrum obtained as in Production Example 1, the product showed a peak of N-H deformation vibration of secondary acid amide at 1,540 cm$^{-1}$ and a peak of C=O stretching vibration at 1,640 cm$^{-1}$. In $^{13}$C-NMR, the product showed a chemical shift of the carbon used for the amide bond at around 172 ppm, and a signal of the 6-position carbon shifted to lower magnetic field due to the opening of the terminal saccharide ring at around 62.7 ppm. These data show that the resultant compound has a structure shown by the above-described compound As. The rest of the reaction mixture was used as it is in the following Production Example 4.

Production Example 4

Synthesis of Compound $Bs_2$ group, a silane agent and a saccharide-bonded silane agent; $m_3$ represents the number of monosaccharide units, which may be 4; and Rb represents methylene, $m_2$ represents 3 and R represents a hydrogen atom or Formula 27).

The reaction mixture obtained in Production Example 3 was added to 3 g of previously activated (by means of vacuum drying at 180° C. for 2 hours) silica gel (produced by YMC Co.; mean pore diameter, 120Å; mean particle size, 5 μm). To this were additionally added 9.6 ml of DMSO and 4 ml of pyridine, and reaction was allowed to proceed at 90° C. for 12 hours. To the resulting reaction mixture was added 4 ml of 4-methylphenyl isocyanate. After 5 hours of stirring at 80° C. the presence of excess isocyanate groups remaining in the reaction mixture was confirmed by the peak of C=N stretching vibration at 2,270 cm$^{-1}$ in its IR spectrum. The resultant silane-treated silica gel contained in the reaction mixture was washed with tetrahydrofuran, methanol, acetone and hexane to remove excess Compound $A_2$, and then dried in vacuum at 60° C. for 2 hours. The thus obtained compound was subjected to IR spectrometry and elementary analysis. Results of the elementary analysis are shown in Table 1.

Its IR spectrum showed a peak of stretching vibration of carbonyl group at 1,710 cm$^{-1}$, which proves the existence of polysaccharide derivatives on silica surface. Thus Compound $Bs_2$ was obtained. In order to improve the properties of the thus obtained Compound $Bs_2$ as a separating agent for chromatography, the compound was subjected to a conventional end capping treatment with trimethylchlorosilane.

The resulting product was filtered with a G4 glass filter, and the residue was washed as above with tetrahydrofuran, methanol, acetone and hexane, and then dried at reduced pressure at 60° C. for 2 hours, to obtain a product to be used as a separating agent for chromatography. The chiral resolution ability of the compound was investigated as a separating agent for various racemic compounds. Results obtained are shown in Table 2.

($Bs_2$)

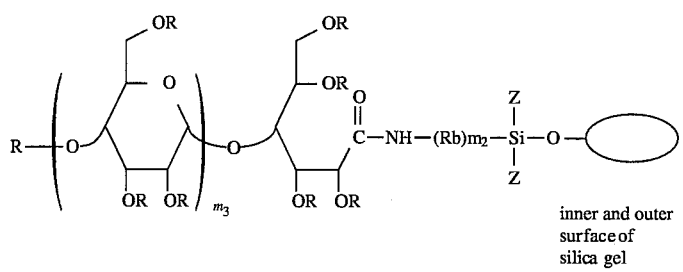

(wherein Z represents a member selected from the group consisting of the surface of a porous carrier, an alkoxy

TABLE 2

| Racemate | Separating Agent | | | | | |
|---|---|---|---|---|---|---|
| | Bs$_2$ | | Bs$_3$ | | Control | |
| | k$_1$ | α | k$_1$ | α | k$_1$ | α |
| ① (structure: O, Ph, Ph) | 0.37 | Δ(+) | 0.60 | 1.16#(+) | 0.37 | Δ#(+) |
| ② (structure with two N and aromatic rings) | 1.57 | X | 0.85 | Δ(−) | 0.54 | Δ(+) |
| ③ (chromanone with Ph) | 2.05 | Δ(+) | 1.17 | Δ(+) | 1.50 | Δ(+) |
| ④ (2-phenylcyclohexanone) | 1.82 | X | 0.85 | 1.07(−) | 0.76 | Δ(−) |
| ⑤ Co(acac)$_3$ | 3.54 | Δ(+) | 1.57 | X | 0.62 | Δ(+) |
| ⑥ (Ph-C(=O)-CH(OH)-Ph) | 1.73 | 1.06(+) | 2.07 | 1.10(+) | 0.88 | 1.08(+) |
| ⑦ (cyclopropane with two CONHPh) | 1.27 | 1.27(+) | 1.22 | 1.26(+) | 0.51 | 1.45(+) |
| ⑧ (C$_6$H$_5$)$_3$C—CHOH—C$_6$H$_5$ | 1.13 | 1.07(+) | 2.95 | 1.14(+) | 0.45 | Δ(+) |

[Notes]
X: Not possible to separate the racemate
Δ: Separation of the racemate was detectable by a rotation detector, but not detectable by a UV detector
(+): A dextro-rotatory compound eluted earlier
(−): A levo-rotatory compound was eluted earlier Production Example 5

Synthesis of Compound A$_3$ (m$_3$=4 in Compound A)

Into 4.4 ml of anhydrous ethylene glycol was dissolved 0.7 g of the lactone obtained in Production Example 3. To this was a 3-aminopropyltriethoxysilane, and reaction was allowed to proceed at 70° C. for 6 hours in a nitrogen stream. Part of the product (about 0.6 ml) was taken out and used as a sample for IR and NMR analyses.

In its IR spectrum obtained as in Production Example 1, the product showed a peak of N-H deformation vibration of secondary acid amide at 1,540 cm$^{-1}$ and a peak of C=O stretching vibration at 1,640 cm$^{-1}$. In $^{13}$C-NMR, the product showed a chemical shift of the carbon used for the amide bond at around 172 ppm, and a signal of the 6-position carbon shifted to lower magnetic field due to the opening of the terminal saccharide ring at around 62.7 ppm. The structure of Compound A$_3$ can be estimated on the basis of these data. The rest of the reaction mixture was used as it is in the following Production Example 6.

Production Example 6 Synthesis of Compound $Bs_3$

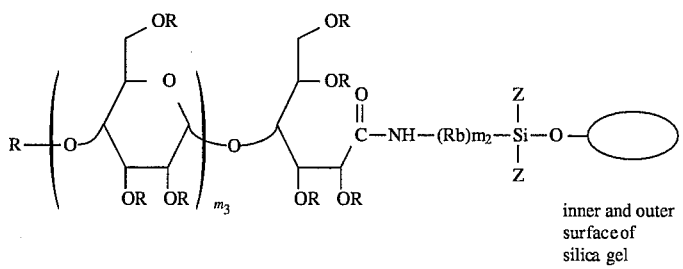

(wherein Z represents a member selected from the group consisting of the surface of a porous carrier, an alkoxy group, a silane agent and a saccharide-bonded silane agent; $m_3$ represents the number of monosaccharide units, which may be 4; and Rb represents methylene, $m_2$ represents 3 and R represents a hydrogen atom or Formula 30).

The reaction mixture obtained in Production Example 5 was added to 3 g of previously activated (by means of vacuum drying at 180° C. for 2 hours) silica gel (produced by YMC Co.; mean pore diameter, 120Å mean particle size, 5 μm). To this were additionally added 9.6 ml of anhydrous ethylene glycol and 4 ml of pyridine, and reaction was allowed to proceed at 90° C. for 12 hours.

The surface-treated silica gel obtained was collected by filtration with a G4 glass filter, washed with DMF, etc., and then dried in vacuum at 70° C. for 3 hours. To 3.7 g of surface-treated silica gel obtained were added 13 ml of DMA and 3 ml of pyridine. Then, 3.7 g of 3,5-dimethylphenyl isocyanate was added thereto and reacted at 80° C. for 12 hours. The presence of excess isocyanate groups remaining in the reaction mixture was confirmed by the peak of C=N stretching vibration at 2,270 cm$^{-1}$ in its IR spectrum.

The resultant surface-treated silica gel contained in the reaction mixture was washed with tetrahydrofuran, methanol, acetone and hexane, and then subjected to IR spectrometry and elementary analysis. Results of the elementary analysis are shown in Table 1.

The compound shows a peak of carbonyl stretching vibration at 1,710 cm$^{-1}$ in its IR spectrum, which proves the existence of polysaccharide derivatives on silica surface. Thus compound $Bs_3$ was obtained.

In order to improve the properties of the thus obtained Compound $Bs_3$ as a separating agent for chromatography, the compound was subjected to a conventional end capping treatment with trimethylchlorosilane. The resulting product was collected by filtration with a G4 glass filter and the residue was washed as above with tetrahydrofuran, methanol, acetone and hexane, and then dried in vacuum at 60° C. for 2 hours, to obtain a product to be used as a separating agent for chromatography. The chiral resolution ability of the compound was investigated as a separating agent for various racemic compounds. Results obtained are shown in Table 2. 3,5-Dimethylphenyl isocyanate used above can be readily obtained from 3,5-dimethylaniline by using phosgene, triphosgene, or the like.

Example 1

(1-1) Synthesis of Compound $A_1$ of the Following Formula

[Compound 24]

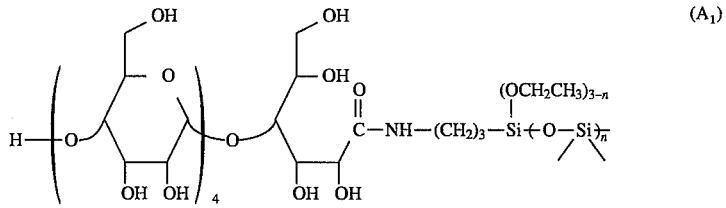

(wherein n has the same meanings as defined above).

Compound $A_1$ was synthesized according to the method described in Japanese Patent Application No. H4-311,042 (311,042/1992), by using 5 g of maltopentose. A peak of N-H deformation vibration of secondary amide is observed at 1,540 cm$^{-1}$ and a peak of C=O stretching vibration is observed at 1,640 cm$^{-1}$ in the IR spectrum of Compound $A_1$ shown in FIG. 2. In $^{13}$C-NMR [solvent, DMSO-d6; concentration of Compound $A_1$, 5%(W/V); standard substance, TMS; 60° C.; 400 MHz], and a peak assignable to carbons in the amide bonds is observed at 172 ppm, peaks assignable to 4- and 6-positioned carbons of open saccharide rings are observed at 82.7 ppm and 62.8 ppm, respectively, peaks assignable to ethoxy carbons in silane moieties are observed at 18.1 ppm and 57.7 ppm, and the peak assignable to the 3-position carbon of the propyl group is shifted to higher magnetic field of 41.0 ppm. These data indicate that the main structure of Compound $A_1$ is the same as that of Compound A described hereinabove.

(1-2) Synthesis of Compound $C_1$ of the Following Formula;

[Compound 25]

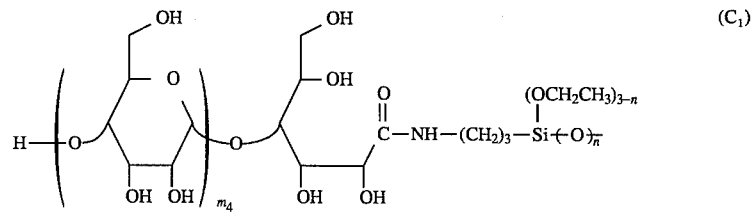

($C_1$)

wherein n has the same meanings as defined above. Mean degree of polymerization ($m_4$) of the compound based on the determination of phosphate=19.

Into 300 ml of sterilized ultra pure water were dissolved 1.2 g of Compound A, synthesized in (1-1) above and 12 g of glucose-1-phosphate (G1P) (pH was adjusted to 6). To this was added 180 units of crude phosphorylase derived from potato, and the resulting mixture was allowed to stand at 30° C. for about 3 hours. The degree of polymerization of the saccharide chain was followed by sampling part of the reaction mixture and, after deactivating the enzyme with trichloroacetic acid, determining the amount of liberated phosphate by the Fiske-Subbarow method.

After the enzyme had been inactivated by heating on a hot water bath, the reaction mixture was filtered. To the filtrate was added 100% ethanol of an amount equal to that of the filtrate, so as to precipitate the saccharide synthesized. The precipitate was washed with 50% ethanol, 100% ethanol and diethyl ether, and then dried in vacuum at 60° C. for 2 hours, to obtain 2.2 g of Compound $C_1$. Thereafter, the product was analyzed by gel filtration liquid chromatography. The mean degree of polymerization ($m_4$) of the product determined from the standard curve based on a standard amylose reagent (produced by Nakano Vineget Co., Ltd.) was 31, and that based on the determination of phosphate was 19.

In $^{13}$C-NMR [solvent, DMSO-d6; concentration of Compound $B_1$, 5%(W/V); standard substance, TMS; 60° C.; 400 MHz], peaks of 1- and 2-position methylene protons derived from the silane agent appear at 0.54 ppm and 1.53 ppm, respectively (the 3-position methylene protons are masked by the protons of the saccharides), and a peak of methyl protons of the ethoxy groups appears at 1.15 ppm (methylene protons are masked by the saccharide protons). These data indicate that the product is Compound $C_1$.

(1-3) Synthesis of Compound of the Following Formula (2);

[Formula 26]

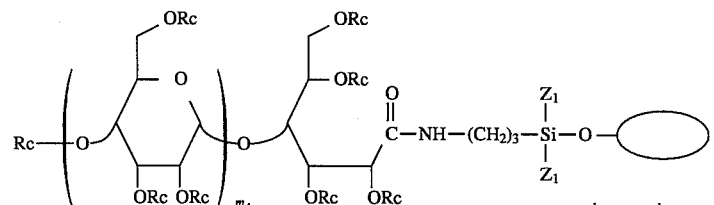

(2)

wherein Rc represents a hydrogen atom or

[Formula 27]

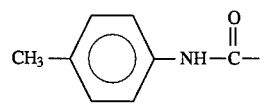

and $Z_1$ represents the surface of silica gel, an ethoxy group, a silane agent, or a polysaccharide-bonded silane agent to a saccharide moiety. Substitution rate based on elementary analysis=41%. $m_4$ is estimated to be roughly the same as that of Compound $C_1$.

Into 14 ml of anhydrous DMSO was dissolved 1.0 g of Compound $C_1$ synthesized in (1-2) above, and the resulting solution was added to 3 g of previously activated (by means of vacuum drying at 180° C. for 2 hours) silica gel (produced by YMC Co.; mean pore size, 12 nm; mean particle size, 5 µm). To this was added 4 ml of pyridine, and the resulting mixture was heated at 90° C. for 12 hours in a nitrogen stream, to allow the silane moiety of the above Compound $C_1$ to chemically bond to the silanol groups of the silica gel.

The thus obtained surface-treated silica gel was collected by filtration with a G4 glass filter and was washed with DMSO, tetrahydrofuran, methanol, acetone and hexane to remove unbonded Compound $C_1$, and then dried in vacuum at 60° C. for 2 hours. The existense of the polysaccharide on silica surface was confirmed by elementary analysis, the results of which were: C, 6.25%; H, 1.53%; and N, 0.06%.

The surface treated silica gel was dispersed into a mixture of 8 ml of anhydrous DMSO and 3 ml of anhydrous pyridine, and 3.0 ml of 4-methylphenyl isocyanate was added thereto and allowed to react at 80° C. for 5 hours in a nitrogen atmosphere, to modify the hydroxyl groups in the saccharide moieties chemically bonded to the surface of silica gel. After the presence of excess isocyanate groups in the reaction mixture had been confirmed by the peak of C=N stretching vibration at 2,270 cm$^{-1}$ in its IR spectrum, the polysaccharide derivative-conjugated silica gel contained in the reaction mixture was washed with tetrahydrofuran, methanol, acetone and hexane to remove impurities, and then dried in vacuum at 60° C. for 2 hours. The resultant compound was then subjected to IR spectrometry and elementary analysis. Results are shown in FIG. and Table 3.

TABLE 3

| Compound | Elementary Analysis | | |
|---|---|---|---|
| | C (%) | H (%) | N (%) |
| Formula (2) | 15.87 | 1.83 | 1.68 |
| Formula (3) | 7.15 | 0.70 | 0.41 |
| Formula (4) | 7.09 | 0.69 | 0.64 |
| Formula (5) | 7.08 | 0.69 | 0.62 |
| Formula (6) | 9.14 | 0.90 | 0.86 |
| Formula (7) | 9.00 | 0.90 | 1.01 |
| Formula (8) | 8.90 | 0.90 | 1.08 |
| Formula (9) | 12.18 | 0.97 | 1.81 |
| Formula (10) | 12.78 | 1.19 | 1.91 |

In its IR spectrum, a peak of carbonyl stretching vibration (C=O absorption of secondary carbamic acid ester) was observed at near 1,730 cm$^{-1}$ and the existence of polysaccharide derivatives on silica surface was confirmed by elementary analysis. Thus a compound of Formula (2) was obtained.

In order to improve the properties of the thus obtained Formula (2) as a separating agent for chromatography, the compound was subjected to a conventional end capping treatment with trimethylchlorosilane.

The thus obtained product was collected by filtration with a G4 glass filter and was washed as above with tetrahydrofuran, methanol, acetone and hexane, and then dried in vacuum at 60° C. for 2 hours, to obtain a product to be used as a separating agent for chromatography. The chiral resolution ability of the compound was investigated as a separating agent for various racemic compounds. Results obtained are shown in Table 4.

In Tables 2 and 4, $k_1$ indicates capacity factor of the isomer eluted fast and is obtained by the following formula; and α indicates separation factor and is obtained from the following equation. $k_2$, likewise $k_1$, indicates capacity factor of the isomer eluted rate and is obtained from the following equation.

$\alpha = k_1/k_2$ $k_1 = $[(retention time of isomer eluted earlier) −(dead time)] /(dead time)

$k_2 = $[(retention time of isomer eluted later) −(dead time)] /(dead time)

TABLE 4

| Racemate | Separating Agent (General Formula) | | | | | | | |
|---|---|---|---|---|---|---|---|---|
| | (2) | | (3) | | (4) | | (5) | |
| | $k_1$ | α | $k_1$ | α | $k_1$ | α | $k_1$ | α |
| ① (Ph-CH(O-)-CH2-Ph epoxide) | 0.68(+) | 1.21 | 0.21(+) | 2.03 | 0.17(+) | 1.96 | 0.16(+) | 1.87 |
| ② (diamine structure) | 4.31(+) | Δ# | 1.37(+) | 1.10 | 0.29(+) | 1.44 | 0.29(+) | 1.42 |
| ③ (chromanone-Ph) | 2.16(+) | 1.06 | 0.57(+) | 1.10 | 0.45(+) | 1.23 | 0.46(+) | 1.25 |
| ④ (2-phenylcyclohexanone) | 2.06(+) | 1.05# | 0.39(−) | Δ | 0.33(−) | Δ | 0.32(−) | Δ |
| ⑤ Co(acac)$_3$ | 3.26(−) | 1.11# | 0.20(−) | Δ | 0.45(+) | Δ | 0.45(+) | Δ |
| ⑥ (Ph-C(=O)-CH(OH)-Ph) | 5.64(−) | Δ | 1.50(−) | 1.08 | 1.25(−) | Δ | 1.20(−) | Δ |

TABLE 4-continued

| | | | | | | | | |
|---|---|---|---|---|---|---|---|---|
| ⑦ ▲(CONHPh, CONHPh) | 1.76(+) | 1.25 | 1.14(+) | 1.30 | 0.79(+) | 1.33 | 0.76(+) | 1.38 |
| ⑧ $(C_6H_5)_3C-CHOH-C_6H_5$ | 1.63(+) | 1.38 | 0.81(+) | 1.81 | 0.59(+) | 2.01 | 0.56(+) | 1.90 |
| ⑨ 2,2'-dihydroxy-6,6'-dimethylbiphenyl | 1.65(−) | 1.40 | 0.88(−) | 1.83 | 0.77(−) | 1.50 | 0.75(−) | 1.48 |

| | Separating Agent (General Formula) | | | | | | | |
|---|---|---|---|---|---|---|---|---|
| | (6) | | (7) | | (8) | | Control | |
| Racemate | $k_1$ | α | $k_1$ | α | $k_1$ | α | $k_1$ | α |
| ① trans-stilbene oxide | 0.24(+) | 2.56 | 0.27(+) | 2.94 | 0.24(+) | 2.94 | 0.42(+) | 3.04 |
| ② Tröger's base | 0.40(+) | 1.56 | 0.33(+) | 1.50 | 0.30(+) | 1.49 | 0.53(+) | 1.58 |
| ③ flavanone | 0.62(+) | 1.33 | 0.55(+) | 1.07 | 0.50(+) | 1.06 | 0.93(+) | 1.12 |
| ④ 2-phenylcyclohexanone | 0.45(−) | Δ | 0.38(−) | Δ | 0.34(−) | Δ | 0.61(−) | Δ |
| ⑤ Co(acac)₃ | 0.64(+) | Δ | 0.15(−) | Δ | 0.15(−) | Δ | 0.25(+) | Δ |
| ⑥ benzoin | 1.83(−) | 1.07 | 1.75(−) | 1.21 | 1.57(−) | 1.20 | 3.14(−) | 1.21 |
| ⑦ ▲(CONHPh, CONHPh) | 1.31(+) | 2.15 | 1.67(+) | 3.35 | 1.48(+) | 3.50 | 3.25(+) | 2.01 |
| ⑧ $(C_6H_5)_3C-CHOH-C_6H_5$ | 1.06(+) | 2.18 | 1.34(+) | 2.28 | 1.21(+) | 2.28 | 2.65(+) | 1.98 |

TABLE 4-continued

| (9) | | 1.16(−) | 1.68 | 1.40(−) | 2.22 | 1.27(−) | 2.20 | 2.46(−) | 2.11 |
|---|---|---|---|---|---|---|---|---|---|

[Notes]
X: Not possible to separate the racemate
Δ: Separation of the racemate was detectable by a rotation detector, but not detectable by a UV detector
(+): A dextro-rotatory compound eluted earlier
(−): A levo-rotatory compound was eluted earlier

Example 2

(2-1) Synthesis of Compound $C_2$ of the Following Formula;

[Formula 28]

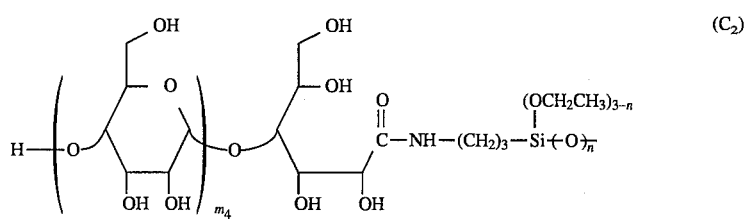

($C_2$)

wherein n has the same meanings as defined above. Mean degree of polymerization ($m_4$) based on the determination of phosphate: 79

Compound $C_2$ of the above formula was synthesized in the same manner as in (1-2) of Example 1. That is, 0.3 g of Compound $A_1$ synthesized in (1-1) of Example 1 and 12 g of glucose-1-phosphate (G1P) were dissolved into a mixture of 105 ml of DMSO and 300 ml of sterilized ultra pure water (pH was adjusted to 6). To this was added 210 units of crude phosphorylase derived from potato, and the resulting mixture was allowed to stand at 30° C. for about 4 hours. The polymerization of the saccharide chain was followed by sampling part of the reaction mixture and, after deactivating the enzyme with trichloroacetic acid, determining the amount of liberated phosphate by the Fiske-Subbarow method.

After the enzyme had been inactivated by heating on a hot water bath, the reaction mixture was filtered. To the filtrate was added ethanol of an amount equal to that of the filtrate, so as to precipitate the saccharide synthesized. The precipitate was washed with 50% ethanol, 100% ethanol and diethyl ether, and then dried in vacuum at 60° C. for 2 hours, to obtain 2.2 g of Compound $C_2$. Thereafter, the product was analyzed by gel filtration liquid chromatography. The mean degree of polymerization ($m_4$) of the product determined from the standard curve based on a standard amylose reagent (produced by Nakano Vineger Co., Ltd.) was 85, and that based on the determination of phosphate was 79.

(2-2) Synthesis of Compound of Formula (3)

[Compound 29]

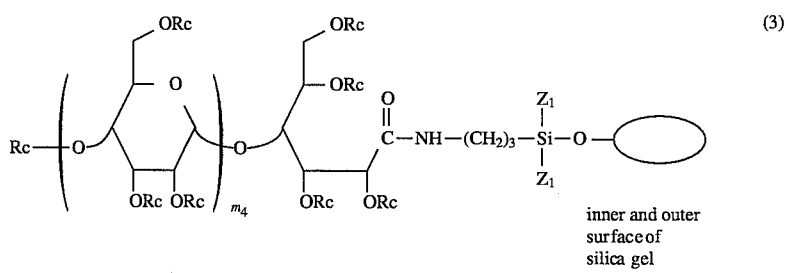

(3)

inner and outer surface of silica gel wherein Rc represents a hydrogen atom or

[Formula 30]

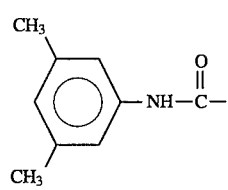

and $Z_1$ has the same meanings as defined above. The substitution degree of hydroxy group from the weight analysis=90% or above. $m_4$ is estimated to be roughly the same as that of Compound $C_2$. Into 14 ml of anhydrous DMSO was dissolved 1.0 g of Compound $C_2$ synthesized in (2-1) above, and the resulting solution was added to 3 g of previously activated (by means of vacuum drying at 180° C. for 2 hours) silica gel (produced by Daiso Co.; mean pore size, 100 nm; mean particle size, 7 μm). To this was added 4 ml of pyridine, and the resulting mixture was heated at 90° C. for 12 hours in a nitrogen stream, to allow the silane moiety of Compound $C_2$ to chemically bond to the silanol groups of the silica gel.

The thus obtained surface-treated silica gel was collected by filtration with a G4 glass filter and the residue was washed with DMSO, tetrahydrofuran, methanol, acetone and hexane to remove unbonded Compound $C_2$, etc. and then dried in vacuum at 60° C. for 2 hours.

The surface-treated silica gel was dispersed into a mixture of 8 ml of anhydrous DMSO and 3 ml of anhydrous pyridine, and 1.5 ml of 3,5-dimethylphenyl isocyanate was added thereto and allowed to react at 80° C. for 5 hours in an nitrogen stream, to modify the hydroxyl groups in the saccharide moieties chemically bonded to the surface of silica gel. After the presence of excess isocyanate groups in the reaction mixture had been confirmed by the peak of C=N stretching vibration at 2,270 $cm^{-1}$ in its IR spectrum, the polysaccharide derivative-conjugated silica gel contained in the reaction mixture was washed with tetrahydrofuran, methanol, acetone and hexane to remove impurities, and then dried in vacuum at 60° C. for 2 hours. The resultant compound was then subjected to IR spectrometry and elementary analysis. Results of elementary analysis are shown in Table 3.

The existence of the polysaccharide derivatives on silica surface was confirmed by the peak of carbonyl stretching vibration (absorption of C=O in the secondary carbamic acid ester) at near 1,730 $cm^{-1}$ in its IR spectrum, as well as by elementary analysis. Thus the compound of Formula (3) was obtained.

In order to improve the properties of the thus obtained compound as a separating agent for chromatography, the compound was subjected to a conventional end capping treatment with trimethylchlorosilane.

The thus obtained product was collected by filtration with a G4 glass filter and was washed as above with tetrahydrofuran, methanol, acetone and hexane, and then dried in vacuum at 60° C. for 2 hours, to obtain a product to be used as a separating agent for chromatography. The chiral resolution ability of the compound was investigated as a separating agent for various racemic compounds. Results obtained are shown in Table 4.

Example 3

(3-1) Synthesis of Lactonized Amylose (1) of the Following Formula;

[Formula 31]

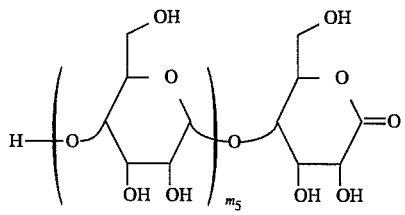

(mean degree of polymerization ms based on the determination of phosphate=15).

A KOH-methanol solution is added to an iodine-methanol solution of 18.9 g maltopentose in accordance with a known method to obtain 19.7 g of potassium {0-α-D-glucopyranosyl-(1→4)}$_4$-D-glucanate (which may hereinafter be referred to as potassium G5 glucanate). Into 800 ml of sterilized ultra pure water was dissolved 2.1 g of the potassium G5 glucanate and 32 g of glucose 1-phosphate (G1P) (pH was adjusted to 6). To this was added 240 units of crude phosphorylase derived from potato, and the resulting mixture was allowed to stand at 45° C. for about 2 hours. The degree of polymerization of the saccharide chain was followed by sampling part of the reaction mixture and, after inactivating the enzyme with trichloroacetic acid, determining the amount of liberated phosphate by the Fiske-Subbarow method.

The enzyme was inactivated by heating on a hot water bath, and the reaction mixture was filtered. Thereafter, the glucanate salt was converted into lactone by adding concentrated hydrochloric acid to the reaction mixture to pH 1. To the resulting reaction mixture was added 100% ethanol of an amount equal to that of the reaction mixture, so as to precipitate the saccharide synthesized. The precipitate was washed with 50% ethanol, 100% ethanol and diethyl ether, and then dried in vacuum at 60° C. for 2 hours, to obtain 3.0 g of lactonized Amylose (1) of the above formula.

The product was analyzed by gel filtration liquid chromatography. The mean degree of polymerization ($m_5$) of the product determined from the standard curve based on a standard amylose reagent (produced by Nakano Vineget Co.,Ltd.) was 37, and that based on the determination of phosphate was 15. In its IR spectrum, a peak of C=O stretching vibration of lactone was observed at 1,740 $cm^{-1}$.

(3-2) Synthesis of Lactonized Amylose (2) of the Following Formula;

[Formula 32]

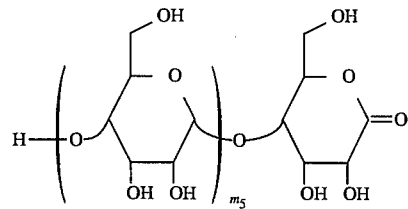

(mean degree of polymerization based on the determination of phosphate=29).

Into a mixture of 240 ml of sterilized ultra pure water and 105 ml of DMSO were dissolved 0.53 g of potassium G5 glucanate and 16 g of glucose 1-phosphate (G1P). After its pH had been adjusted to 6,400 units of crude phosphorylase derived from potato was added thereto, and the resulting mixture was allowed to stand at 45° C. for about 2 hours. The degree of polymerization of the saccharide chain was followed by sampling part of the reaction mixture and, after deactivating the enzyme with trichloroacetic acid, determining the amount of liberated phosphate by the Fiske-Subbarow method.

The enzyme was inactivated by heating on a hot water bath, and the reaction mixture was filtered. Thereafter, the glucanate salt was converted into lactone by adding concentrated hydrochloric acid to the reaction mixture to pH 1. To the resulting reaction mixture was added 100% ethanol of an amount equal to that of the reaction mixture, so as to precipitate the saccharide synthesized. The precipitate was washed with 50% ethanol, 100% ethanol and diethyl ether, and then dried in vacuum at 60° C. for 2 hours, to obtain 3.0 g of lactonized Amylose (2) of the above formula.

The product was analyzed by gel filtration liquid chromatography. The mean degree of polymerization ($m_5$) of the product determined from the standard curve based on a standard amylose reagent (produced by Nakano Vineget Co.,Ltd.) was 47, and that based on the determination of phosphate was 29.

(3-3) Synthesis of Lactonized Amylose (3) of the Following Formula;

[Formula 33]

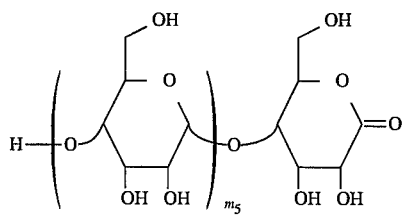

(mean degree of polymerization ms based on the determination of phosphate=92).

Into a mixture of 240 ml of sterilized ultra pure water and 105 ml of DMSO were dissolved 0.265 g of potassium G5 glucanate synthesized in (3-1) above and 16 g of glucose 1-phosphate (G1P). After its pH had been adjusted to 6,550 units of crude phosphorylase derived from potato was added thereto, and the resulting mixture was allowed to stand at 45° C. for about 5 hours. The degree of polymerization of the saccharide chain was followed by sampling part of the reaction mixture and, after inactivating the enzyme with trichloroacetic acid, determining the amount of liberated phosphate by the Fiske-Subbarow method.

The enzyme was inactivated by heating on a hot water bath, and the reaction mixture was filtered. Thereafter, the glucanate salt was converted into lactone by adding concentrated hydrochloric acid to the reaction mixture to pH 1. To the resulting reaction mixture was added 100% ethanol of an amount equal to that of the reaction mixture, so as to precipitate the saccharide synthesized. The precipitate was washed with 50% ethanol, 100% ethanol and diethyl ether, and then dried in vacuum at 60° C. for 2 hours, to obtain 2.48 g of lactonized Amylose (3) of the above formula.

The product was analyzed by gel filtration liquid chromatography. The mean degree of polymerization ($m_5$) of the product determined from the standard curve based on a standard amylose reagent (produced by Nakano Vineger Co., Ltd.) was 147, and that based on the determination of phosphate was 92.

(3-4) Synthesis of Surface-Treated silica Gel (No. 1)

To 10 g of previously activated (by means of vacuum drying at 180° C. for 2 hours) silica gel (produced by Daiso Go.; mean pore diameter, 100 μm; particle size, 7 μm) were added 36 ml of anhydrous benzene and 3 ml of anhydrous pyridine. Then, 2 ml of 3-amin opropyltriethoxysilane was added thereto and allowed to react at 90° C. for 12 hours.

The thus obtained surface-treated silica gel was washed with methanol, acetone and hexane, and then dried in vacuum at 60° C. for 2 hours.

(3-5) Synthesis of Surface-Treated silica Gel (No. 2)

To 10 g of previously activated (by means of vacuum drying at 180° C. for 2 hours) silica gel (produced by Daiso Co.; mean pore diameter, 100 μm; particle size, 7 μm) were added 12 ml of anhydrous benzene and 1 ml of anhydrous pyridine. Then, 0.7 ml of 3-(2-aminoethylaminopropyl)trimethoxysilane was added thereto and allowed to react at 90° C. for 12 hours.

The thus obtained surface-treated silica gel was washed with methanol, acetone and hexane, and then dried in vacuum at 60° C. for 2 hours.

(3-6) Synthesis of Surface-Treated silica Gel (No. 3)

To 10 g of previously activated (by means of vacuum drying at 180° C. for 2 hours) silica gel (produced by Daiso Co.; mean pore diameter, 100 μm; particle size, 7 μm) were added 12 ml of anhydrous benzene and 1 ml of anhydrous pyridine. Then, 0.7 ml of 3-(2-aminoethylaminoethylamino)propyltrimethoxysilane was added thereto and allowed to react at 90° C. for 12 hours. The thus obtained surface-treated silica gel was washed with methanol, acetone and hexane, and then dried in vacuum at 60° C. for 2 hours.

(3-7) Synthesis of compound of the Following Formula (4)

To 3 g of the aminopropyl functionalized silica gel obtained in (3-4) was added a solution prepared by dissolving 1 g of lactonized Amylose (1) into 8 ml of anhydrous DMSO, and reaction was allowed to proceed at 80° C. for 12 hours to form amide bonds. The resulting polysaccharides-conjugated silica gel was collected by filtration with a G4 glass filter and was washed with DMSO, tetrahydrofuran, methanol, acetone and hexane to remove the excess lactonized Amylose (1), etc. and dried in vacuum at 60° C. for 2 hours.

Subsequently, the polysaccharides-conjugated silica gel was dispersed into a mixture of 8 ml of anhydrous DMSO and 3 ml of anhydrous pyridine, and then 1.5 ml of 3,5-dimethylphenyl isocyanate was added thereto and allowed to react at 80° C. for 5 hours. The presence of excess isocyanate groups in the reaction mixture was confirmed by the peak of C═N stretching vibration at 2,270 cm$^{-1}$ in its IR spectrum. The polysaccharides-conjugated silica gel contained in the reaction mixture was washed with tetrahydrofuran, methanol, acetone and hexane and then dried in vacuum at 60° C. for 2 hours. The resultant compound Formula (4) was then subjected to IR spectrometry and elementary analysis. Results of elementary analysis are shown in Table 3.

The existence of polysaccharide derivatives on silica surface was confirmed by the carbonyl stretching vibration (absorption of C═O in the secondary carbamic acid ester) at near 1,730 cm$^{-1}$ in its IR spectrum, as well as by elementary analysis. Thus the compound of Formula (4) was obtained. The chiral resolution ability of the compound was investigated as a chromatographic separating agent for various racemic compounds. Results obtained are shown in Table 4.

[Formula 34]

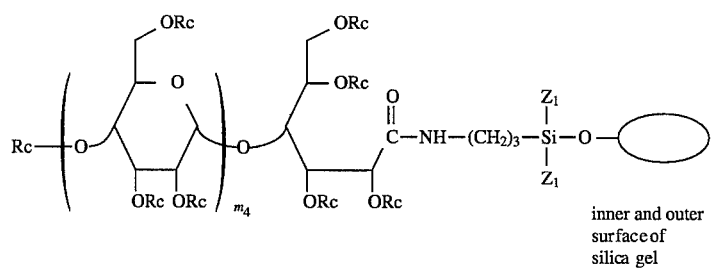

(4)

wherein Rc represents a hydrogen atom or

[Formula 35]

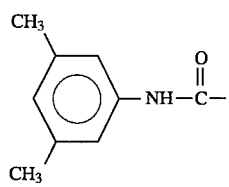

and $Z_1$ has the same meanings as defined above. The substitution degree of hydroxyl groups from weight analysis=90% or above. $m_4$ is estimated to be roughly the same as ms of Compound $C_5$.

Example 4

Synthesis of Compound of the Following Formula (5);

[Formula 36]

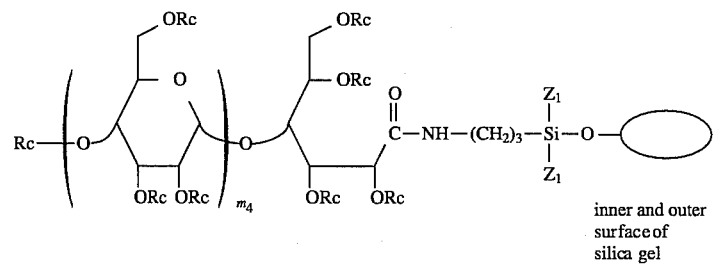

(5)

wherein Rc represents

[Formula 37]

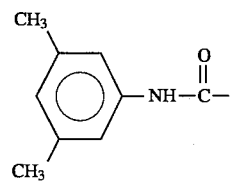

and $Z_1$ has the same meanings as defined above. The substitution degree of hydroxyl groups from weight analysis=90% or above. $m_4$ is estimated to be roughly the same as $m_5$ of lactonized Amylose (2).

To 3 g of aminopropyl functionalized silica gel obtained in (3-4) of Example 3 was added a solution prepared by dissolving 1 g of lactonized Amylose (2) into 8 ml of anhydrous DMSO, and reaction was allowed to proceed at 80° C. for 12 hours to form amide bond. The resulting polysaccharides-conjugated silica gel was collected by filtration with a G4 glass filter and was washed with DMSO, tetrahydrofuran, methanol, acetone and hexane to remove excess lactonized Amylose (2), etc. and dried in vacuum at 60° C. for 2 hours.

Subsequently, the polysaccharides-conjugated silica gel was dispersed into a mixture of 8 ml of anhydrous DMSO and 3 ml of anhydrous pyridine, and then 1.5 ml of 3,5-dimethylphenyl isocyanate was added thereto and allowed to react at 80° C. for 5 hours. The presence of excess isocyanate groups in the reaction mixture was confirmed by the peak of C=N stretching vibration at 2,270 cm$^{-1}$ in its IR spectrum. The polysaccharides derivatives conjugated silica gel contained in the reaction mixture was washed with tetrahydrofuran, methanol, acetone and hexane and then dried in vacuum at 60° C. for 2 hours. The resultant compound was subjected to IR spectrometry and elementary analysis. Results of elementary analysis are shown in Table 3.

The existence of the polysaccharide derivatives was confirmed by the carbonyl stretching vibration (absorption of C=O in the secondary carbamic acid ester) at near 1,730 cm$^{-1}$ in its IR spectrum, as well as by elementary analysis. Thus the compound of the above described Formula (5) was obtained. The chiral resolution ability of the compounds was investigated as a chromatographic separating agent for various racemic compounds. Results obtained are shown in Table 4.

Example 5

Synthesis of Compound of the Following Formula (6);

[Formula 38]

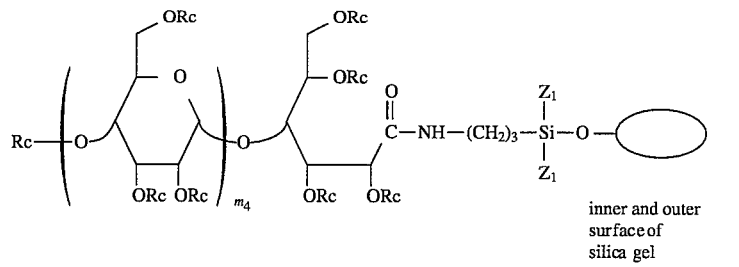

(6)

wherein Rc represents

[Formula 39]

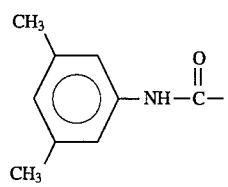

and $Z_1$ has the same meanings as defined above. The substitution degree of hydroxyl groups from weight analysis=90% or above. $m_4$ is estimated to be roughly the same as $m_5$ of lactonized Amylose (3).

To 3 g of aminopropyl functionalized silica gel obtained in (3-4) of Example 3 was added a solution prepared by dissolving 1 g of lactonized Amylose (3) into 8 ml of anhydrous DMSO, and reaction was allowed to proceed at 80° C. for 12 hours to form amide bonds. The resulting polysaccharides-conjugated silica gel was collected by filtration with a G4 glass filter and was washed with DMSO, tetrahydrofuran, methanol, acetone and hexane to remove excess lactonized Amylose (3), etc. and dried in vacuum at 60° C. for 2 hours.

Subsequently, the polysaccharides-conjugated silica gel was dispersed into a mixture of 8 ml of anhydrous DMSO and 3 ml of anhydrous pyridine, and then 1.5 ml of 3,5-dimethylphenyl isocyanate was added thereto and allowed to react at 80° C. for 5 hours. The presence of excess isocyanate groups in the reaction mixture was confirmed by the peak of C=N stretching vibration at 2,270 cm$^{-1}$ in its IR spectrum. The polysaccharide derivatives-conjugated silica gel contained in the reaction mixture was washed with tetrahydrofuran, methanol, acetone and hexane and then dried in vacuum at 60° C. for 2 hours. The resultant compound was subjected to IR spectrometry and elementary analysis. Results of elementary analysis are shown in Table 3.

The existence of polysaccharide derivatives on silica surface was confirmed by the carbonyl stretching vibration (absorption of C=O in the secondary carbamic acid ester) at near 1,730 cm$^{-1}$ in its IR spectrum, as well as by elementary analysis. Thus the compound of the above described Formula (6) was obtained. The chiral resolution ability of the compounds was investigated as a chromatographic separating agent for various racemic compounds. Results obtained are shown in Table 4.

Example 6

Synthesis of Compound of the Following Formula (7);

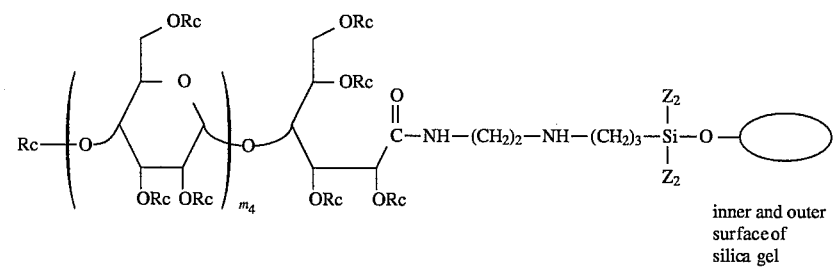

(7)

wherein Rc represents a hydrogen atom or

[Formula 41]

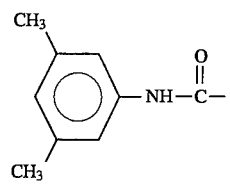

and $Z_2$ represents the surface of silica gel, a methoxy group, a silane agent or a saccharide-bonded silane agent. Substitution degree of hydroxyl groups from the weight analysis= 90% or above. $m_4$ is estimated to be roughly the same as $m_5$ of lactonized Amylose (3)3.

To 3 g of the amino groups functionalized silica gel obtained in (3-5) of Example 3 was added a solution prepared by dissolving 1 g of lactonized Amylose (3) synthesized in a similar manner as in (3-3) of Example 3 into 8 ml of anhydrous DMSO, and reaction was allowed to proceed at 80° C. for 12 hours to form amide bonds. Thereafter, the procedure of Example 5 was followed to obtain a compound of the above-described General Formula (7). The chiral resolution ability of the compounds was investigated as a chromatographic separating agent for various racemic compounds. Results obtained are shown in Table 4.

Example 7

Synthesis of Compound of the Following Formula (8);

[Formula 42]

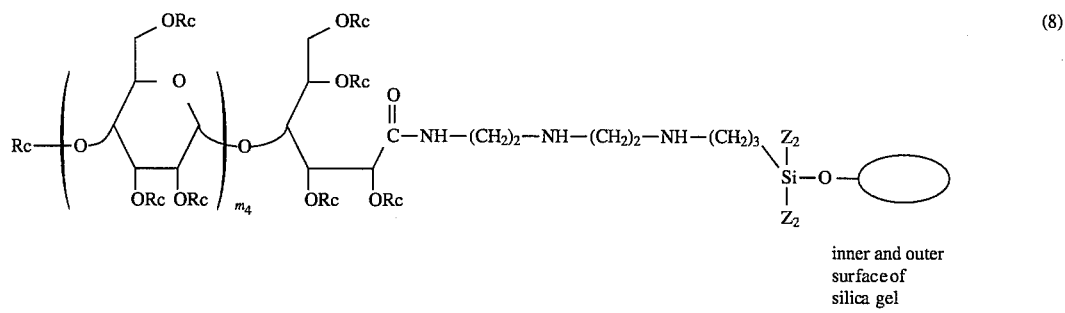
(8)

wherein Rc represents a hydrogen atom or

[Formula 43]

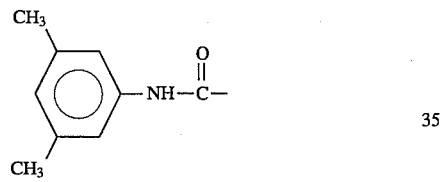

and $Z_2$ has the same meanings as defined above. Substitution degree of hydroxyl group from the weight analysis: 90% or above. $m_4$ is estimated to be roughly the same as $m_5$ of lactonized Amylose (3)).

To 3 g of the amino groups-fanctionalized silica gel obtained in (3-6) of Example 3 was added a solution prepared by dissolving 1 g of lactonized Amylose (3) synthesized in a similar manner as in (3-3) of Example 3 into 8 ml of dried DMSO, and reaction was allowed to proceed at 80° C. for 12 hours to form amide bonds. Thereafter, the procedure of Example 5 was followed to obtain a compound of the above-described Formula (8). The chiral resolution ability of the compound was investigation as a chromatographic separating agent for various racemic compounds. Results obtained are shown in Table 4.

Example 8

Synthesis of Compound of the Following Formula (9);

[Compound 44]

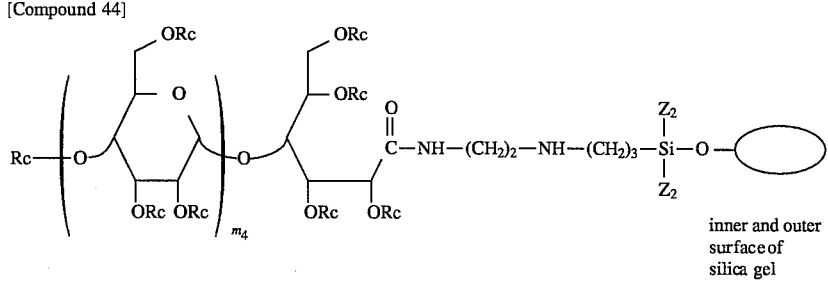
(9)

wherein Rc represents a hydrogen atom or

[Compound 45]

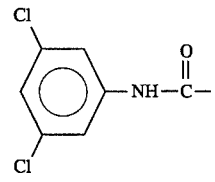

degree of hydroxyl group from the weight analysis is 90% or above; $m_4$ is estimated to be roughly the same as $m_5$ of lactonized Amylose (3); and $Z_2$ represents any of the surface of silica gel, a methoxy group, a silane agent and a saccharide-bonded silane agent.

(8-1) Synthesis of Surface-Treated Silica Gel:

To 10 g of silica gel (made by Fuji Silicia Co.—having a mean pore size of 50 nm and a mean particle size of 5 μm) that had been previously activated (by drying in vacuum at 180° C. for 2 hours), added were 12 ml of anhydrous benzene and 1 ml of anhydrous pyridine. 0.7 ml of 3-(2-aminoethylaminopropyl)triethoxysilane were added thereto and reacted at 90% for 12 hours.

The amino groups-functionalized silica gel thus obtained was washed with methanol, acetone and hexane and dried in vacuum at 60° C. for 2 hours.

(8-2)

To 8 g of the amino groups-functionalized silica gel, obtained in (8-1) above, added was a solution obtained by dissolving 1 g of lactonized Amylose (3) that had been produced in the same manner as in Example 3 (3-3) in 8 ml of anhydrous DMSO, and reaction was allowed to proceed at 80° C. for 12 hours to form amide bonds. The resulting surface-treated silica gel was collected by filtration through a G4 glass filter, and the residue was washed with DMSO, tetrahydrofuran, methanol, acetone and hexane to remove the excess lactonized Amylose (3), etc. and dried in vacuum at 60° C. for 2 hours.

The saccharide-bonded silica gel was dispersed into a mixture of 8 ml of anhydrous DMA-LiCl and 3 ml of pyridine, and 5 g of 3,5-dichlorophenyl isocyanate (this was formed from 3,5-dichloroaniline by an ordinary method) dissolved in 5 ml of DMA were added thereto and reacted at 80° C. in nitrogen for 12 hours. The presence of excess isocyanate groups in the reaction mixture was confirmed by the peak of C=N stretching vibration at 2,270 cm$^{-1}$ in its IR spectrum. The saccharide-bonded, surface-treated silica gel was washed with tetrahydrofuran, methanol, acetone and hexane and dried in vacuum at 60° C. for 2 hours. The resultant compound was then subjected to IR spectrometry and elementary analysis. Results of elementary analysis are shown in Table 1.

The formation of bonding to silica gel, or the production of the compound of Formula (9) set forth above was confirmed by the carbonyl stretching vibration (absorption of C=O in the secondary carbamic acid ester) at 1,710 cm$^{-1}$ in its IR spectrum, as well as by elementary analysis. The compound was tested and evaluated with respect to its function as a chromatographic separating agent for various racemic compounds. Results obtained are shown in Table 5.

TABLE 5

| Racemate | Separate Agent | | | |
|---|---|---|---|---|
| | Formula (9) | | Control | |
| | $k_1$ | α | $k_1$ | α |
| (10) ![structure with NO2, CH3OCO, COO-piperidine-CH2C6H5, pyridine ring with CH3, N-H, CH3] | 1.90(−) | 1.29✗ | 0.42(+) | Δ |
| (11) ![structure with NO2, CH3OCO, COO(CH2)2NCH3, CH2C6H5, CH3, N-H, CH3] | 2.42(−) | 1.18✗ | 0.66(−) | Δ |

[Notes]
Δ: Separation of the racemate was detectable by a rotation detector, but not detectable by a UV detector
(−): A levo-rotatory compound was eluted earlier
✗: An eluent→hexane:THF = 80:20

Example 9

Synthesis of Compound of the Following Formula (10);

[Compound 46]

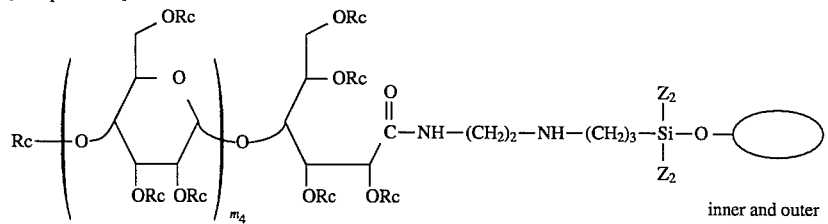

(10)

inner and outer surface of silica gel wherein Rc represents a hydrogen atom or

[Compound 47]

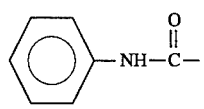

substitution degree of hydroxyl group from the weight analysis is 90% or above; $m_4$ is estimated to be roughly the same as ms of lactonized Amylose (3); and $Z_2$ represents any of the surface of silica gel, a methoxy group, a silane agent and a saccharide-bonded silane agent).

To 3 g of the amino groups functionalized silica gel obtained in Example 8 (8-1), added was a solution obtained by dissolving 1 g of lactonized Amylose (3) that had been produced in the same manner as in Example 3 (3-3) in 8 ml of dry DMSO, and reaction was allowed to proceed at 80° C. for 12 hours to form amide bonds. The resulting surface-treated silica gel was collected by filtration through a G4 glass filter, and the residue was washed with DMSO, tetrahydrofuran, methanol, acetone and hexane to remove the excess lactonized Amylose (3), etc. and dried in vacuum at 60° C. for 2 hours.

The saccharide-bonded silica gel was dispersed into a mixture of 8 ml of anhydrous DMA-LiCl and 3 ml of pyridine, and 2 ml of phenyl isocyanate were added thereto and reacted at 80° C. for 12 hours in nitrogen. The presence of excess isocyanate groups in the reaction mixture was confirmed by the peak of C=N stretching vibration at 2,270 $cm^{-1}$ in its IR spectrum. The saccharide-bonded, surface-treated silica gel was washed with tetrahydrofuran, methanol, acetone and hexane and dried in vacuum at 60° C. for 2 hours. The resultant compound was then subjected to IR spectrometry and elementary analysis. Results of elementary analysis are shown in Table 1.

The formation of bonding to silica gel, or the production of the compound of Formula (10) set forth above was confirmed by the carbonyl stretching vibration (absorption of C=O in the secondary carbamic acid ester) at 1,710 $cm^{-1}$ in its IR spectrum, as well as by elementary analysis. The compound was tested and evaluated with respect to its function as a chromatographic separating agent for various racemic compounds. Results obtained are shown in Table 6.

TABLE 6

| Racemate | Separate Agent | | | |
|---|---|---|---|---|
| | Formula (10) | | Control | |
| | $k_1$ | α | $k_1$ | α |
| (3) 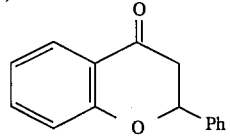 | 2.18(+) | 1.60 | 0.93(+) | 1.12 |
| (5) Co(acac)$_3$ | 2.44(−) | 1.31 | 0.25(+) | Δ |

[Notes]
Δ: Separation of the racemate was detectable by a rotation detector, but not detectable by a UV detector
(+): A dextro-rotatory compound eluted earlier
(−): A levo-rotatory compound was eluted earlier

Application Example

Preparation of Column for Optical Resolution and Optical Resolution Power

The novel substances obtained in Examples 1 to 9 were packed into empty, stainless steel columns of 0.46 cm×25 cm, by the slurry packing method. For the packing was used PS-10 and PS-20 Autopacking Systems manufactured by Kyoto Chromato Co. The chiral resolution powder of the substances was evaluated by high performance liquid chromatography, using the columns, a Waters 515 Pump, a 484 UV Detector, etc. As a control was cited a separating agent prepared by physically coating an amylose tris (3,5-dimethylphenyl carbamate) derivative onto aminopropyl functionalized silica gel. Results cited are shown in Table 2, 3 and 4 [see Chemistry Letters, pp. 1857–1860 (1987)]. The results shown in Table 2 show that any of the compounds represented by Formulae (6), (7) and (8) obtained in Examples 5, 6 and 7 give particularly improved a-values for Racemates (7) and (8), in comparison with the control. The results shown in Table 3 show that the compound represented by Formula (9) could be separated ,by using an eluate containing tetrahydrofuran, Racemates (10) and (11) which could not be separated with the compound of Comparative Example. Further, the results shown in Table 4 show that the compound represented by Formula (10) could be separated Racemate (5) which could not be separated with the compound of Comparative Example. The α-values for Racemate (3) was improved remarkably in comparison with the control.

To examine the solvent resistance of the chiral resolution columns prepared by using the novel substances according to the present invention, a tetrahydrofuran (THF) solution was passed though the columns at a flow rate of 1 ml/min for 2 hours and thereafter the optical resolution powder of the columns was measured. No changes were recognized. This proves that the substances have excellent solvent resistance.

The above analysis was carried out by using an eluent of hexane/IPA (=90/10) at room temperature. # denotes 90:5 and ·X· denotes an eluent→hexane/THF=80:20, respectively. The flow rate was 0.5 ml/min.

As explained hereinabove, the novel substances of the present invention have excellent solvent resistance and are useful as a chromatographic separating agent for separating chiral compounds substances. In addition, the novel substances can be efficiently produced in a convenient manner in accordance with the present invention.

What is claimed is:

1. A substance having the following formula (1) comprising a polysaccharide compound which is chemically bonded to the inner and outer surfaces of a porous carrier at a reducing terminal of said polysaccharide compound

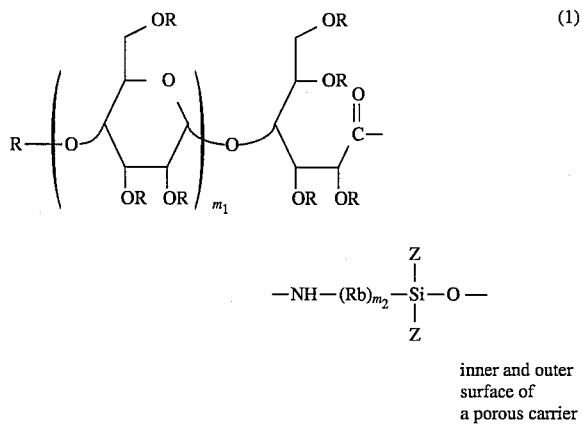

wherein R represents Ra, —CO—Ra or —CO—NH—Ra, in which Ra represents a hydrogen atom or a substituent selected from the group consisting of a substituted or unsubstituted alkyl group, a substituted or unsubstituted phenyl group and a substituted or unsubstituted heterocyclic residue; Rb represents a substituted or unsubstituted methylene group, a substituted or unsubstituted phenylene group or a group containing at least one covalently bonded hetero atom; each Z independently represents a member selected from the group consisting of a surface of a porous carrier, a halogen atom, an alkyl group, an alkoxy group, a phenyl group, and a silane agent; $m_1$ represents the number of monosaccharide units and is a number from 10 to 500; and $m_2$ represents an integer of from 1 to 20.

2. A method of producing a substance of the formula (1) according to claim 1, comprising:

(a) contacting an oligosaccharide having a degree of polymerization from 3 to 10 with a silane agent to chemically bond the oligosaccharide to the silane agent at a reducing terminal of the oligosaccharide, (b) polymerizing the oligosaccharide from step (a) to an average degree of polymerization from 11 to 500 in the presence of an enzyme, and (c) contacting the resulting polysaccharide compound from step (b) with a porous carrier to chemically bond the polysaccharide compound to the porous carrier at the silane at the reducing terminal of the polysaccharide compound.

3. A method of producing a substance of the formula (1) according to claim 1, comprising:

(a) oxidizing an oligosaccharide having an aldehyde group present at a reducing terminal of the oligosaccharide, the oligosaccharide having a degree of polymerization from 3 to 10 with an oxidizing agent, (b) polymerizing the saccharide chain of the resulting oxidized product to a degree of polymerization from 11 to 500 in the presence of an enzyme, and adding an acid to form a polysaccharide.

4. The method of producing a substance according to claim 2 or 3, wherein said enzyme is a member selected from the group consisting of hydrolases, saccharide transferases and polymerases.

5. The method of producing a novel substance according to claim 2 or 3, wherein said enzyme is phosphorylase.

6. The method of producing a novel substance according to claim 2 or 3, wherein said enzyme is phosphorylase and dimethylsulfoxide is added to the resulting reaction mixture upon enzymatic reaction using said enzyme.

7. The method of producing a novel substance according to claim 2 or 3, wherein substituents are present in all or part of the hydroxyl groups of the saccharide moieties by ether, ester or urethane bonds.

8. In a chromatography method including passing a material to be separated through a separating agent, the improvement comprising the separating agent being said substance according to claim 1.

9. The substance according to claim 1, wherein Z is a silane agent which is a saccharide-bonded silane agent.

10. The substance according to claim 1, wherein the porous carrier is selected from the group consisting of silica gel, diatomaceous earth, porous glass, hydroxyapatite, alumina, titanium oxide, magnesia, polyacrylamide and polyacrylate.

11. The substance according to claim 1, wherein the porous carrier is silica gel.

12. The substance according to claim 11, wherein the silica gel has a particle size of 1 to 1,000 μm and a mean pore size of 10Å to 100 μm; and the amount of the polysaccharide compound is 5 to 50 weight %, based on the weight of the silica gel.

13. The substance according to claim 1, wherein Ra is selected from the group consisting of hydrogen, methyl, ethyl, propyl, t-butyl, phenyl, methylphenyl, dimethylphenyl, ethylphenyl, diethylphenyl, trimethylsilylphenyl, alkoxyphenyl, dialkoxyphenyl, halogenated phenyl, dihalogenated phenyl, phenylazophenyl, naphthyl, anthryl, pyridyl and furyl.

14. The substance according to claim 1, wherein R is

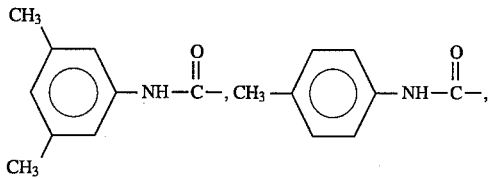

-continued

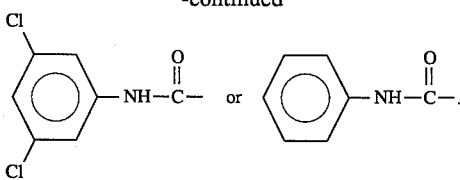

15. The substance according to claim 1, wherein Z is a silane agent selected from the group consisting of

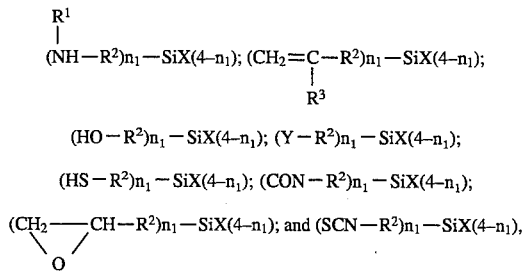

wherein $n_1$ is 1 to 3; $R^1$ is a hydrogen atom or a $C_1$–$C_{20}$ alkyl group; $R^2$ is a $C_1$–$C_{20}$ alkyl group; X is a substituted or unsubstituted $C_1$–$C_{10}$ alkoxy group, a halogen atom, a hydroxyl group or a substituted or unsubstituted phenoxy group; and Y is a hydrogen atom.

16. The substance according to claim 1, wherein R is —CO—NH—Ra, Ra is 3,5-dimethylphenyl and $m_1$ is 90 to 500.

17. The substance according to claim 16, wherein Rb is $(CH_2)_2$—NH—$(CH_2)_3$, $m_2=1$ and Z is $OCH_3$.

18. The substance according to claim 16, wherein Rb is $(CH_2)$, $m_2$ is 3 and Z is $OCH_2CH_3$.

19. The method of claim 2, wherein the oligosaccharide has a degree of polymerization of 3 to 10 and is selected from the group consisting of α-1,4-glucan oligomers, β-1,4-glucan oligomers, α-1,6-glucan oligomers, β-1,6-glucan oligomers, α-1,3-glucan oligomers, β-1,3-glucan oligomers, α-1,2-glucan oligomers, β-1,2-glucan oligomers, β-1,4-chitooligosaccharides, β-1,4-N-acetylchitooligosaccharides, β-1,4-galactans, α-1,6-galactans, β-2,1-fructans, β-2,6-fructans, β-1,4-xylans, β-1,3-xylans, β-1,4-mannans and α-1,6-mannans; the enzyme is selected from the group consisting of phosphorylase, dextransucrase, levansucrase and pullulanase; the porous carrier is selected from the group consisting of silica gel, diatomaceous earth, porous glass, hydroxyapatite, alumina., titanium oxide, magnesia, polyacrylamide and polyacrylate; and the silane agent contains an amino group.

20. The method of claim 3, wherein the oligosaccharide has a degree of polymerization of 3 to 10 and is selected from the group consisting of α-1,4-glucan oligomers, β-1,4-glucan oligomers, α-1,6-glucan oligomers, β-1,6-glucan oligomers, α-1,3-glucan oligomers, β-1,3-glucan oligomers, α-1,2-glucan oligomers, β-1,2-glucan oligomers, β-1,4-chitooligosaccharides, β-1,4-N-acetylchitooligo-saccharides, β-1,4-galactans, α-1,6-galactans, β-2,1-fructans, β-1,6-fructans, β-1,4-xylans, β-1,3-xylans, β-1,4-mannans and α-1,6-mannans; the enzyme is selected from the group consisting of phosphoxylase, dextransucrase, levansucrase and pullulanase; and the porous carrier is selected from the group consisting of silica gel, diatomaceous earth, porous glass, hydroxyapatite, alumina, titanium oxide, magnesia, polyacrylamide and polyacrylate.

21. The method of claim 2, which further comprises after step (c), introducing a group of the formula Ra, —CO—Ra or —CO—NH—Ra wherein Ra is selected from the group consisting of an unsubstituted alkyl group, a substituted alkyl group, an unsubstituted phenyl group, a substituted phenyl group, an unsubstituted heterocyclic residue and a substituted heterocyclic residue, to replace one or more hydrogen atoms in one or more hydroxyl groups in the polysaccharide, said polysaccharide having the following formula:

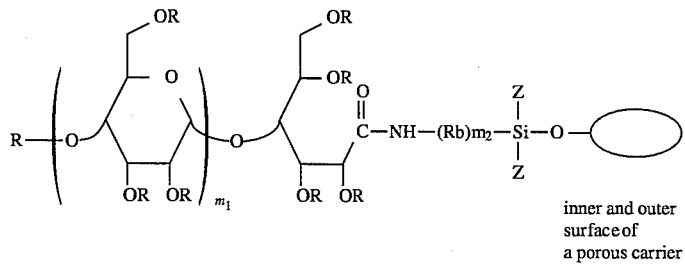

inner and outer surface of a porous carrier wherein R is a hydrogen atom, Rb is a substituted or unsubstituted methylene group, a substituted or unsubstituted phenylene group or a group containing at least one covalently bonded hetero atom; each Z independently is a member selected from the group consisting of a surface of a porous carrier, a halogen atom, an alkyl group, an alkoxy group, a phenyl group, and a silane agent; $m_1$ is the number of monosaccharide units and is a number from 10 to 500; and $m_2$ is an integer of from 1 to 20.

22. The method of claim 3, which further comprises after step (b):

(c) contacting a silane agent with a porous carrier to chemically bind the silane agent to the porous carrier, (d) contacting the porous carrier which is chemically bound to the silane agent with the polysaccharide from step (b), the polysaccharide having the following formula

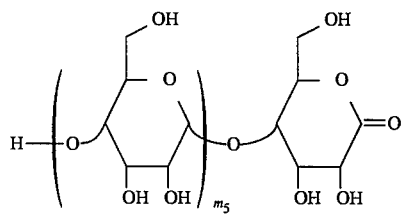

wherein $m_5$ is the mean degree of polymerization, to chemically bind the polysaccharide to the porous carrier chemically bound to the silane agent, and (e) introducing a group of the formula Ra, —CO—Ra or —CO—NH—Ra wherein Ra is selected from the group consisting of an unsubstituted alkyl group, a substituted alkyl group, an unsubstituted phenyl group, a substituted phenyl group, an unsubstituted heterocyclic residue and a substituted heterocyclic residue, to replace one or more hydrogen atoms in one or more hydroxyl groups in the polysaccharide.

* * * * *